US006793920B2

(12) United States Patent  
Nagano et al.

(10) Patent No.: US 6,793,920 B2  
(45) Date of Patent: Sep. 21, 2004

(54) ANTITHROMBOTIC AGENT AND ANTI-VON WILLEBRAND FACTOR MONOCLONAL ANTIBODY

(75) Inventors: Mitsuyo Nagano, Kawasaki (JP); Hiroshi Yamamoto, Kawasaki (JP); Morikazu Kito, Kawasaki (JP); Ryota Yoshimoto, Kawasaki (JP); Tsuyoshi Kobayashi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 217 days.

(21) Appl. No.: 09/923,952

(22) Filed: Aug. 8, 2001

(65) Prior Publication Data

US 2002/0028204 A1 Mar. 7, 2002

Related U.S. Application Data

(62) Division of application No. 09/299,016, filed on Apr. 26, 1999, now Pat. No. 6,280,731, which is a division of application No. 08/836,982, filed as application No. PCT/JP95/02435 on Nov. 29, 1995, now Pat. No. 5,916,805.

(30) Foreign Application Priority Data

Nov. 19, 1994 (JP) .............................................. 6-297070

(51) Int. Cl.$^7$ ........................ A61K 39/395; C07K 16/36

(52) U.S. Cl. ............................... 424/145.1; 424/130.1; 424/141.1; 435/326; 435/337; 435/346; 530/387.1; 530/388.1; 530/388.2; 530/388.25

(58) Field of Search ........................... 464/130.1, 141.1, 464/172.1; 435/326, 346; 530/387.1

(56) References Cited

U.S. PATENT DOCUMENTS

| 5,202,264 | A |   | 4/1993 | Benson et al. |
| 5,744,584 | A | * | 4/1998 | Scarborough |
| 5,916,805 | A |   | 6/1999 | Nagano et al. |
| 6,280,731 | B1 | * | 8/2001 | Nagano et al. |

FOREIGN PATENT DOCUMENTS

EP    0 799 891 A1    10/1997

OTHER PUBLICATIONS

H. Yamamoto, et al., "Monoclonal Antibody Against Von Willebrand Factor Inhibits Thrombus Formation Without Prolongation of Bleeding", *Blood*, 1995, vol. 86, No. 10,, Supplement 1.

Y. Fujimura, et al., "The Interaction of Botrocetin With Normal or Variant Von Willebrand Factor (Types IIA and IIB) and its Inhibition by Monoclonal Antibodies That Block Receptor Binding", *Thombosis and Haemostasis*, 1992, vol. 68, No. 4, pp. 464–469.

Y. Fujimura, et al., "Studies on Anti–Von Willebrand Factor (vWF) Monoclonal Antibody NMC–4, Which Inhibits Both Ristocetin– And Botrocetin–Induced vWF Binding to Platelet Glycoprotein Ib", *Blood*, Jan. 1, 1991, vol. 77, No. 1, pp. 113–120.

F. Rotblat, et al., "Immunologic Studies of Factor VIII Coagulant Activity (VIII:C) 2 Factor VIII in Selected Vertebrates", *Thrombosis Research*, 1982, vol. 25, pp. 423–431.

G. Piétu, et al., "Production in Escherichia–Coli of a Biologically Active Subfragment of Von Willebrand Factor Corresponding to the Platelet Glycoprotein Ib Collagen; and Heparin Binding Domains", *Biochemical and Biophysical Research Communications*, 1989, vol. 164, No. 3, pp. 1339–1347.

M. Aihara, et al., "Glycoprotein Ib has a Partial Role in Platelet–Von Willebrand Factor Collagen Interaction", *Thrombosis Haemostasis*, 1988, vol. 60, No. 2, pp. 182–187.

S. Jorieux, et al., "Characterization of a Monoclonal Antibody to Von Willebrand Factor as a Potent Inhibitor of Ristocetin–Mediated Platelet Interaction and Platelet Adhesion", *Thombosis Haemostasis*, 1987, pp. 278–282.

H. V. Stel, et al., "Von Willebrand Factor in the Vessel Wall Mediates Platelet Adherence", *Blood*, Jan. 1985, vol. 65, No. 1, pp. 85–90.

J. J. Sixma, et al., "Functional Domains on Von Willebrand Factor Recognition of Discrete Tryptic Fragments by Monoclonal Antibodies That Inhibit Interaction of Von Willebrand Factor With Platelets and With Collagen", *Journal Clinical Investigation*, Sep. 1984, vol. 74, pp. 736–744.

J. A. Katzman, et al., "Monoclonal Antibodies to Von Willebrand's Factor: Reactivity with Procine and Human Antigens", *Blood*, Sep. 1981, vol. 58, No. 3, pp. 530–536.

S. Kobayashi, et al., "Intrahepatic Peribiliary Vascular Plexus in Various Hepatobiliary Diseases: A Histological Survey", *Human Pathology*, Sep. 1994, vol. 25, No. 9, pp. 940–946.

T. W. Chow, et al., "Shear Stress–Induced Von Willebrand Factor Binding to Platelet Glycoprotein Ib Initiates Calcium Influx Associated With Aggregation", *Blood*, Jul. 1992, vol. 80, No. 1, pp. 113–120.

S. Goto, et al., Circulation, vol. 86, No. 6, pp. 1859–1863, "Epinephrine Augments Von Willebrand Factor–Dependent Shear–Induced Platelet Aggregation", Dec. 1992.

(List continued on next page.)

*Primary Examiner*—Phillip Gambel  
(74) *Attorney, Agent, or Firm*—Oblon, Spivak, McClelland, Maier & Neustadt, P.C.

(57) ABSTRACT

A monoclonal antibody, which has reactivity with human von Willebrand factor, which has action to inhibit RIPA (ristocetin-induced platelet aggregation), BIPA (botrocetin-induced platelet aggregation), and SIPA (shear stress-induced platelet aggregation) of human platelet, and which does not express bleeding action in an medicinally effective dose to exhibit antithrombotic action, is used as an active ingredient of an antithrombotic agent.

7 Claims, 14 Drawing Sheets

OTHER PUBLICATIONS

Y. Cadroy, et al., Blood, vol. 83, No. 11, pp. 3218–3224, "Relative Antithrombotic Effects of Nonoclonal Antibodies Targeting Different Platelet Glycoprotein–Adhesive Molecule Interactions in Nonhuman Primates," Jun. 1, 1994.

S. Kageyama, et al., British Journal of Pharmacology, vol. 122, pp. 165–171, "Anti–Thrombotic Effects and Bleeding Risk of AJvW–2, A Monoclonal Antibody Against Human Von Willebrand Factor," 1997.

* cited by examiner

Effects of Respective Antibodies on Binding of Biotinylated AJvW-1 to Immobilized vWF Effects of Respective Antibodies on Binding of Biotinylated AJvW-2 to Immobilized vWF

- —○— Antibody 1
- —●— Antibody 2
- —△— Antibody 3
- —▲— Antibody 4
- —□— NMC-4

FIG. 17

Effects of Respective Antibodies on Binding of Biotinylated AJvW-3 to Immobilized vWF

- —○— Antibody 1
- —●— Antibody 2
- —△— Antibody 3
- —▲— Antibody 4
- —□— NMC-4

FIG. 18

Effects of Respective Antibodies on Binding of Biotinylated AJvW-4 to Immobilized vWF Effects of Respective Antibodies on Binding of Biotinylated NMC-4 to Immobilized vWF

ANTITHROMBOTIC AGENT AND ANTI-VON WILLEBRAND FACTOR MONOCLONAL ANTIBODY

CROSS-REFERENCE TO RELATED APPLICATIONS

This application is a division of U.S. application Ser. No. 09/299,016, filed Apr. 26, 1999 (now U.S. Pat. No. 6,280,731), which is a division of U.S. application Ser. No. 08/836,982, filed Jun. 27, 1997 (now U.S. Pat. No. 5,916,805), which is a 37 C.F.R. §1.371 continuation of PCT International Application PCT/JP95/02435, filed Nov. 29, 1995.

TECHNICAL FIELD

The present invention relates to a novel monoclonal antibody against human von Willebrand factor, which causes no bleeding episodes in a medicinally effective dose to exhibit its antithrombotic action. The present invention also relates to a hybridoma which produces the foregoing monoclonal antibody, and an antithrombotic agent containing the foregoing monoclonal antibody as an active ingredient.

BACKGROUND ART

When a subendothelium is exposed due to an injury of vessel walls in a living body, platelets flowing through the bloodstream immediately adhere to the subendothelim. This triggers a series of platelet activation processes including platelet aggregation and release of intracellular granules, after which thrombus is formed, and thus bleeding is arrested. Accordingly, thrombus formation is necessary and indispensable for the physiological hemostatic mechanism. However, on the other hand, the thrombus causes thrombotic diseases such as myocardial infarction, angina pectoris, cerebral infarction, and cerebral thrombosis which become to hold higher ranks of the cause of death in proportion to the aging of society. Such a situation is recognized as a serious problem.

Many antithrombotic agents have been hitherto developed in order to cure and prevent the thrombotic diseases. However, problems to be solved remain in that many of the conventional antithrombotic agents still have low curative effectiveness in clinical application, they have low specificity to thrombus, and they cause hemorrhagic tendency as a side effect. One of the causes of such circumstances is considered as follows. Namely, almost all of the antithrombotic agents are designed only for the purpose of inhibiting the platelet-activating process. A method for measuring platelet aggregation in vitro, which provides an index of the activity, is insufficient to reflect the complicated thrombus formation process in vivo.

Thrombus formation proceeds in accordance with specific binding between glycoprotein on platelet membrane and subendothelium or proteins in plasma. Especially, glycoprotein IIb/IIIa (hereinafter abbreviated as "GPIIb/IIIa") on platelet membrane functions as a receptor for fibrinogen in the final stage of the thrombus formation. Accordingly, it is expected that GPIIb/IIIa-antagonists may be used as a potent antithrombotic agent. The fibrinogen-binding site on GPIIb/IIIa includes an RGD primary sequence of amino acids. As a result of synthesis and evaluation of many RGD derivatives, it has been confirmed that GPIIb/IIIa antagonist exhibits the antithrombotic effect by strongly inhibiting the platelet aggregation, according to an animal models in vivo and clinical investigations (*Thrombosis and Haemostasis*, vol. 69, p. 560, 1993). However, a problem emerges in that GPIIb/IIIa antagonists simultaneously suppress the normal hemostatic mechanism, and hence the hemorrhagic tendency as a side effect appears more strongly as compared with the conventional antithrombotic agents (*The Lancet*, vol. 343, p. 881, 1994; *The New England Journal of Medicine*, vol. 330, p. 956, 1994).

On the other hand, those known as important proteins which function at the early stage of thrombus formation include glycoprotein Ib on platelet membrane (hereinafter abbreviated as "GPIb") and von Willebrand factor in blood plasma (hereinafter abbreviated as "vWF"). Hemorrhagic lesions associated with occurrence of qualitative and quantitative change in vWF include von Willebrand disease (hereinafter referred to as "vWD"). A clinical knowledge has been obtained that serious bleeding scarcely occurs in vWD patients as compared with patients of thrombasthenia (hemorrhagic disease due to deficiency of GPIIb/IIIa). Therefore, a possibility is conceived that powerful antithrombotic action may be exhibited without involving the hemorrhagic tendency by inhibiting the interaction between GPIb and vWF. However, only a monoclonal antibody and a low molecular weight compound ATA (Aurin Tricarboxylic Acid; *Blood*, vol. 72, p. 1898, 1988) have been known as substances to specifically inhibit the interaction between GPIb and vWF. Any antithrombotic action of the anti-GPIb monoclonal antibody in vivo has not been confirmed. Instead, side effects are emphasized in that the anti-GPIb monoclonal antibody causes thrombocytopenia, and it prolongs the bleeding time (*Blood*, vol. 70, 344a, 1987; *Jpn. J. Clin. Pathol.*, vol. 40, p. 266, 1992). Further, it has been reported for those which antagonize vWF that ATA described above and a mouse anti-swine vWF monoclonal antibody BB3-BD5 exhibit antithrombotic efficacies in an in vivo experiment with animals (*Circulation*, vol. 81, p. 1106, 1990). However, side effects cannot be neglected in the case of both ATA and BB3-BD5. Namely, ATA exhibits the antithrombotic action by inhibiting the interaction between GPIb and vWF, while ATA simultaneously involves completely opposite side effects such that it enhances platelet aggregation and release reaction caused by the aid of collagen, arachidonic acid, A23187, PAF, and $TXA_2$ (*Thrombosis and Haemostasis*, vol. 68, p. 189, 1992). On the other hand, BB3-BD5 exhibits a strong hemorrhagic tendency in its antithrombotic dose (*Proc. Natl. Acad. Sci. USA*, vol. 84, p. 8100, 1987; *SURGERY*, vol. 112, p. 433, 1992).

As described above, there is a dilemma in the existing antithrombotic agents in that the antithrombotic action as an medicinal effect cannot be separated from the hemorrhagic tendency as a side effect (there is no difference between the medicinally effective amount and the amount to cause the side effect).

Recently, shear stress-induced platelet aggregation (hereinafter abbreviated as "SIPA") attracts attention, as closely related to thrombus formation in a pathological state. The vascular diameter is small, and the bloodstream has a large velocity in arteriosclerosis lesions and small arteries. Therefore, a high shear stress occurs in such regions due to the interaction between vessel wall and blood. In such a situation, vWF in blood is activated, and its tertiary structure is changed. As a result, vWF plays a crucial role in thrombus formation. Namely, the following process is known. Firstly, vWF existing on subendothelium binds to GPIb on platelet membrane, and thus platelets adhere to vessel wall. Secondly, vWF existing in blood plasma cross-links glycoprotein IIb/IIIa on platelet membrane, and thus the platelet aggregation reaction is allowed to proceed. Consequently, thrombus formation finally occurs.

It is generally known that an antibiotic ristocetin or a snake venom botrocetin allows vWF to cause a change in tertiary structure in vitro, equivalent to the change under a high shear stress. Namely, in the presence of ristocetin or botrocetin, vWF acquires the binding ability to GPIb. Methods for measuring the physiological activity of vWF in vitro by utilizing the foregoing characteristic include ristocetin-induced platelet aggregation (hereinafter abbreviated as "RIPA") and botrocetin-induced platelet aggregation (hereinafter referred to as "BIPA"), as well as a method for measuring binding of vWF to GPIb in the presence of ristocetin or botrocetin. The foregoing methods are widely utilized. Owing to the progress of experimental techniques, an apparatus has been also developed, in which SIPA is measured in vitro by actually applying a shear stress. It is considered that an identical domain on vWF involved in the binding to GPIb in any of the reactions.

Several antibodies against vWF, which inhibit the activity of vWF in vitro, have been hitherto obtained. However, many of them are inferior in reaction specificity, and almost all of them do not inhibit the botrocetin-dependent reaction, even though they inhibit the ristocetin-dependent reaction. As described above, it is considered that the GPIb-binding site on vWF induced by ristocetin is homologous to that induced by botrocetin. Therefore, the foregoing antibodies possibly recognize the binding site on vWF for ristocetin or botrocetin. Strictly speaking, it is possible to say that they do not inhibit the physiological activity of vWF, and hence they have low reaction specificities. In such circumstances, it has been reported that two antibodies, i.e., NMC-4 produced by Fujimura et al. (J. Nara Med. Assoc., vol. 36, p. 662, 1985) and RFF-VIIIRAG:1 produced by Tuddenham et al., inhibit in vitro the reaction depending on both of ristocetin and botrocetin (Blood, vol. 17, No. 1, p. 113, 1991).

It has been reported that epitopes for the two antibodies exist in the GPIb-binding site of the vWF molecule, and they are located between 449th and 728th amino acid residues of an amino acid sequence of the vWF molecule. Further, binding of iodine-labeled NMC-4 to vWF is partially inhibited by RFF-VIIIRAG:1. According to this fact, it is considered that the both epitopes are located at positions considerably close to one another. Moreover, RFF-VIIRAG:1 inhibits BIPA only partially, while NMC-4 completely inhibits BIPA. For this reason, studies have been diligently made in the scientific field of vWF by using NMC-4, and certain results have been obtained. Among animals other than human, NMC-4 has its reactivity only with rat vWF.

When a monoclonal antibody against human vWF is prepared in order to obtain information on the GPIb-binding site of human vWF, or in order to use the monoclonal antibody as a preventive agent and a therapeutic agent against diseases relevant to vWF, it is considered to be desirable to prepare the monoclonal antibody as one having high specificity to human vWF.

On the other hand, when a new medicine is developed in an ordinary manner, it is unallowable to perform any test with human without previously performing a test with animals. When a test is performed in relation to physiological activities of vWF and anti-vWF monoclonal antibodies in vivo, it is necessary to use a monoclonal antibody which makes it possible to perform a test with animals, i.e., a monoclonal antibody simultaneously having reactivity with vWF of an animal other than human. By the way, GPIIb/IIIa antagonists, which strongly suppresses human platelet aggregation by the aid of fibrinogen, are not effective on rat (*Thrombosis and Haemostasis*, vol. 70, p. 531, 1993). Further, rat does not cause ristocetin-induced aggregation.

According to these facts, it is generally considered that the mechanism of thrombus formation greatly differs between rat and human. Therefore, it is almost meaningless to evaluate the antithrombotic action of any anti-vWF antibody by using rat. On the contrary, in the case of guinea pig, platelet aggregation is suppressed by GPIIb/IIIa antagonists. Further, ristocetin-induced aggregation is also induced in the same manner as human. Accordingly, it is considered that guinea pig is most suitable as an animal thrombus model for in vivo experiments when the antithrombotic action is evaluated.

According to the foregoing viewpoints, any of a monoclonal antibody having reactivity with only human vWF, and a monoclonal antibody having reactivity with both human vWF and guinea pig vWF is useful. However, such anti-human vWF monoclonal antibodies are not known.

Further, an anti-human vWF monoclonal antibody, which has been confirmed to have antithrombotic action in vivo, is not known.

BRIEF SUMMARY OF THE INVENTION

The present invention provides, in part, a pharmaceutical composition having antithrombotic efficacy containing a pharmaceutically acceptable carrier and a monoclonal antibody having the following properties:

(a) the monoclonal antibody binds to human von Willebrand Factor; and (b) the monoclonal antibody inhibits binding between a monoclonal antibody produced by hybridoma and human von Willebrand Factor, wherein the hybridoma is selected from the group consisting of FERM BP-5248 (AJvW-2). FERM BP-5250 (AJvW-4) or a variant of the hybridoma.

DISCLOSURE OF THE INVENTION

The present invention has been made taking the foregoing viewpoints into consideration, an object of which is to provide monoclonal antibodies against human von Willebrand factor, especially a monoclonal antibody having reactivity with only human vWF, and a monoclonal antibody having reactivity with human vWF as well as guinea pig vWF, which do not express bleeding action in an medicinally effective dose sufficient to express antithrombotic action, hybridomas for producing the foregoing monoclonal antibodies, and an antithrombotic agent containing, as an active ingredient, any one of the foregoing monoclonal antibodies.

The present inventors have succeeded in obtaining a monoclonal antibody having reactivity with human von Willebrand factor and having action to inhibit RIPA, BIPA, and SIPA of human platelet, by immunizing a mouse with human vWF, and fusing spleen cells of the immunized mouse with mouse myeloma cells to prepare a hybridoma. Further, the present inventors have found out that the monoclonal antibody exhibits strong antithrombotic action without involving bleeding in an in vivo thrombosis model. Thus the present invention has been completed.

Namely, the present invention lies in an antithrombotic agent comprising, as an active ingredient, a monoclonal antibody which has reactivity with human von Willebrand factor, which has action to inhibit RIPA (ristocetin-induced platelet aggregation), BIPA (botrocetin-induced platelet aggregation), and SIPA (shear stress-induced platelet aggregation) of human platelet, and which does not express bleeding action in an medicinally effective dose to exhibit antithrombotic action.

In another aspect, the present invention provides a monoclonal antibody having the following properties:

(a) the monoclonal antibody has reactivity with human von Willebrand factor;

(b) the monoclonal antibody inhibits RIPA (ristocetin-induced platelet aggregation), BIPA (botrocetin-induced platelet aggregation), and SIPA (shear stress-induced platelet aggregation) of human platelet;

(c) the monoclonal antibody inhibits RIPA (ristocetin-induced platelet aggregation) and BIPA (botrocetin-induced platelet aggregation) of guinea pig platelet; and (d) the monoclonal antibody exhibits strong antithrombotic action in vivo in guinea pig, but it does not cause bleeding.

In still another aspect, the present invention provides a monoclonal antibody having the following properties:

(A) the monoclonal antibody has reaction specificity to human von Willebrand factor;

(B) the monoclonal antibody inhibits RIPA (ristocetin-induced platelet aggregation), BIPA (botrocetin-induced platelet aggregation), and SIPA (shear stress-induced platelet aggregation) of human platelet; and (C) the monoclonal antibody does not react with von Willebrand factors of rat, guinea pig, and rabbit.

In still another aspect, the present invention provides a hybridoma for producing the monoclonal antibody having the foregoing properties, formed by fusion between spleen cell of a mouse immunized with von Willebrand factor and Sp2/0-Ag14 mouse myeloma cell.

The present invention will be explained in detail below.

<1> Monoclonal Antibody of the Present Invention

A first embodiment of the monoclonal antibody of the present invention (hereinafter referred to as "first monoclonal antibody") lies in a monoclonal antibody having the following properties:

(a) the monoclonal antibody has reactivity with human von Willebrand factor;

(b) the monoclonal antibody inhibits RIPA (ristocetin-induced platelet aggregation), BIPA (botrocetin-induced platelet aggregation), and SIPA (shear stress-induced platelet aggregation) of human platelet;

(c) the monoclonal antibody inhibits RIPA (ristocetin-induced platelet aggregation) and BIPA (botrocetin-induced platelet aggregation) of guinea pig platelet; and (d) the monoclonal antibody exhibits strong antithrombotic action in vivo in guinea pig, but it does not cause bleeding.

A specified embodiment of the monoclonal antibody described above is exemplified by a monoclonal antibody further having the following properties in addition to the foregoing properties:

(e) the monoclonal antibody inhibits BIPA (botrocetin-induced platelet aggregation) of rat platelet; and (f) the monoclonal antibody inhibits BIPA (botrocetin-induced platelet aggregation) of rabbit platelet.

Namely, the first monoclonal antibody of the present invention has high reaction specificity in that it is reactive with human vWF, it has high affinity thereto, and it strongly inhibits any of RIPA, BIPA, and SIPA in vitro. On the other hand, the first monoclonal antibody of the present invention inhibits at least RIPA and BIPA of guinea pig. A monoclonal antibody obtained in Examples described later on further inhibits BIPA of rat and rabbit in vitro. According to an experiment of single intravenous administration to guinea pig, the monoclonal antibody inhibits RIPA and BIPA ex vivo without affecting hematological parameters and coagulation parameters at all. The monoclonal antibody prolongs the time required for femoral artery obstruction in a photochemically reaction-induced thrombosis model based on the use of guinea pig, and it prolongs the time required for obstruction in an arteriovenous shunt formation model. Moreover, when the monoclonal antibody is used in its medicinally effective dose, its effect continues for a long period of time without expressing elongation of bleeding time.

No monoclonal antibody having the properties as described above has been hitherto known. The first monoclonal antibody of the present invention is a novel monoclonal antibody. The first monoclonal antibody of the present invention is clearly different in epitope from NMC-4 described above not only in that it reacts with animal vWF but also in that it does not inhibit binding of NMC-4 to vWF at all (see Examples described later on). The fact that the monoclonal antibody of the present invention has strongly suppressed thrombus formation without involving the bleeding tendency in an in vivo thrombosis model strongly suggest the possibility that the monoclonal antibody of the present invention can be also utilized as an ideal therapeutic agent for thrombotic diseases. The monoclonal antibody of the present invention is not only novel but also industrially applicable.

Namely, the first monoclonal antibody of the present invention is not only useful to specify the GPIb-binding site of vWF. But the first monoclonal antibody of the present invention is also expected to be used as means for analyzing distribution and existing forms of vWF in vivo, and researching the cause of vWD (von Willebrand disease), and to be utilized as a preventive agent and a therapeutic agent effective on thrombotic diseases. Further, the first monoclonal antibody of the present invention can be preferably used for in vivo experiments based on the use of guinea pig when the antithrombotic action is evaluated.

A second embodiment of the monoclonal antibody of the present invention (hereinafter referred to as "second monoclonal antibody") is a monoclonal antibody having the following properties:

(A) the monoclonal antibody has reaction specificity to human von Willebrand factor;

(B) the monoclonal antibody inhibits RIPA (ristocetin-induced platelet aggregation), BIPA (botrocetin-induced platelet aggregation), and SIPA (shear stress-induced platelet aggregation) of human platelet; and (C) the monoclonal antibody does not react with von Willebrand factors of rat, guinea pig, and rabbit.

Namely, the second monoclonal antibody of the present invention is reactive with human vWF, and it has high affinity thereto. Further, the second monoclonal antibody strongly inhibits any of RIPA, BIPA, and SIPA in vitro. Besides, the second monoclonal antibody does not react with any of vWF's of rat, guinea pig, and rabbit. In view of these points, the second monoclonal antibody has specificity much higher than that of NMC-4.

No monoclonal antibody having the properties as described above has been also hitherto known. The second monoclonal antibody of the present invention is a novel monoclonal antibody. The second monoclonal antibody is clearly different in epitope from NMC-4 described above not only in that it does not react with rat vWF but also in that it does not inhibit binding of NMC-4 to vWF at all (see Examples described later on). According to the fact that the monoclonal antibody of the present invention does not react with vWF's of those other than human, for example, vWF of rat, it is assumed that the monoclonal antibody of the present invention recognizes a special antigenic determinant specific to human, the antigenic determinant having been not conserved during the process of evolution. This fact is considered to support the high specificity of the monoclonal antibody of the present invention. The monoclonal antibody of the present invention is not only novel but also industrially applicable.

The second monoclonal antibody specifically and strongly inhibits binding between human vWF and GPIb on platelet membrane. Accordingly, the second monoclonal antibody can be utilized as means for specifying the GPIb-binding site of human vWF, analyzing distribution and existing forms of human vWF in vivo, and researching the cause of vWD (von Willebrand disease), in the same manner as the first monoclonal antibody. No in vivo thrombus formation-suppressing experiment has been performed based on the use of animal, because the second monoclonal antibody does not react with vWF's of animals other than human. However, as demonstrated in Examples described later on, an epitope for the second monoclonal antibody to recognize vWF is located in the vicinity of an epitope recognized by the first monoclonal antibody. Accordingly, the second monoclonal antibody highly possibly recognizes the same epitope as that recognized by the first monoclonal antibody. Therefore, it is assumed that the second monoclonal antibody has an effect equivalent to that of the first monoclonal antibody in vivo. The second monoclonal antibody is expected to be utilized as a preventive agent and a therapeutic agent effective on thrombotic diseases.

The first and second monoclonal antibodies also have action to inhibit shear stress-induced platelet adhesion (hereinafter referred to as "SIPAd") of human platelet. SIPAd also relates to thrombus formation in a pathological state. According to an experiment based on the use of normal human blood, it has been confirmed that the first and second monoclonal antibodies inhibit SIPAd in a dose-dependent manner. Such inhibition has not been observed for GIIb/IIIa antagonists which are expected to be used as antithrombotic agents at present.

A third embodiment of the monoclonal antibody of the present invention is a monoclonal antibody which has reactivity with human vWF, and which has action to inhibit binding between the first or second monoclonal antibody and vWF factor when the third monoclonal antibody is allowed to co-exist with the first or second monoclonal antibody. As demonstrated in Examples described later on, one of the first and second monoclonal antibodies mutually inhibits binding of the other to vWF, using epitopes located closely near to one another or using an identical epitope. Further, the first monoclonal antibody has strongly suppressed thrombus formation without accompanying the hemorrhagic tendency in an in vivo thrombus model. According to these facts, the properties possessed by the first and second monoclonal antibodies that the antibodies inhibit RIPA, BIPA, and SIPA, and they exhibit antithrombotic action, but they do not cause bleeding, are considered to originate from the epitope or opitopes recognized by the antibodies. Therefore, it is considered that the monoclonal antibody, which has the action to inhibit binding between vWF factor and the first and second monoclonal antibodies, can be also as an active ingredient of the antithrombotic agent of the present invention.

The monoclonal antibody having the properties described above can be used as a pharmaceutical. The pharmaceutical specifically includes, for example, an antithrombotic agent as described later on.

<2> Production of Hybridoma and Monoclonal Antibody of the Present Invention

The monoclonal antibody of the present invention is obtained by performing cell fusion between antibody-producing cells of an animal immunized with human vWF and myeloma cells to form hybridomas, cloning a hybridoma capable of producing a monoclonal antibody having reaction specificity to human vWF and inhibiting RIPA, BIPA, and SIPA of human platelet, and culturing the hybridoma or a variant thereof.

Each type of the monoclonal antibodies is obtained as follows. Namely, the first monoclonal antibody is obtained by cloning a hybridoma capable of producing a monoclonal antibody which inhibits RIPA and BIPA of guinea pig platelet, and culturing the hybridoma or a variant thereof. The second monoclonal antibody is obtained by cloning a hybridoma capable of producing a monoclonal antibody which does not react with vWF's of rat, guinea pig, and rabbit, and culturing the hybridoma or a variant thereof.

The hybridoma can be prepared in accordance with a method of Köhler and Milstein (*Nature*, pp. 495–492, 1975). A method for preparing hybridomas, and a method for selecting a hybridoma capable of producing an objective monoclonal antibody will be explained below.

Antibody-producing cells are obtained by immunizing an animal, for example, Balb/c mouse with human vWF, and preparing, from the animal, antibody-producing cells such as spleen cells, lymph node cells, and peripheral blood. Human vWF can be obtained by purification from human blood plasma by means of, for example, gel filtration.

The antibody-producing cells are collected from the animal immunized with human vWF to perform cell fusion with myeloma cells. Cell strains originating from various mammals can be utilized as the myeloma cells to be used for cell fusion. However, it is preferable to use a cell strain originating from an animal of the same species as that of the animal used to prepare the antibody-producing cells. In order to distinguish fused cells from unfused cells after the cell fusion, it is preferable to use a myeloma cell strain having a marker so that unfused myeloma cells cannot survive, and only hybridomas can proliferate. For example, a hybridoma, which is formed by cell fusion between a myeloma cell resistant to 8-azaguanine and an antibody-producing cell as a normal cell, is capable of proliferation in a medium (HAT medium) containing hypoxanthine, aminopterin, and thymidine, while the myeloma cell resistant to 8-azaguanine dies in the HAT medium, and the normal antibody-producing cell cannot be cultured for a long period. Therefore, only the hybridoma can be selectively cultured (*Science*, vol. 145, p. 709, 1964). It is preferable to use, as the myeloma cell, a strain which does not secrete inherent immunoglobulin, from a viewpoint that the objective antibody is easily obtained from a culture supernatant of the hybridoma.

Cell fusion is performed, for example, as follows. Spleen cells of a mouse immunized with human vWF are mixed with mouse myeloma cells, for example, Sp2/0-Ag14 (8-azaguanine resistant, IgG-non-secreting) in the logarithmic growth phase so that the ratio of the spleen cells to the myeloma cells is about 10:1 to 1:1. After centrifugation, a residual precipitate is added with polyethylene glycol having an average molecular weight of 1,000 to 6,000 to give a final concentration of 30 to 50% so that the cells are fused. Fusion may be performed by applying an electric pulse to a mixed solution of the cells, in place of the addition of polyethylene glycol.

Cells having been subjected to the fusion treatment are suspended in HAT medium, for example, Dulbeco's modified Eagle's minimum essential medium (hereinafter abbreviated as "DMEM medium") containing hypoxanthine, aminopterin, thymidine, and 10% fetal bovine serum. The suspension is dispensed and poured into a 96-well microtiter plate or the like, and cells are cultured at 37° C. in 5% carbon dioxide so that only hybridomas are allowed to glow.

The hybridomas obtained as described above are provided as a mixed culture containing a hybridoma which produces the objective monoclonal antibody, in addition to hybridomas which produce monoclonal antibodies against other proteins contained in the human vWF preparation in a mixed manner, or monoclonal antibodies against sites of human vWF irrelevant to RIPA, BIPA, and SIPA. Accordingly, a strain, which produces the objective monoclonal antibody, is selected from the foregoing hybridomas.

The hybridoma, which produces the monoclonal antibody having reactivity with human vWF, can be selected in accordance with enzyme immunoassay based on the use of human vWF as an antigen. A strain, which produces a monoclonal antibody to inhibit both of RIPA and BIPA mediated by human vWF, is selected by measuring the inhibiting activity on RIPA and BIPA by using a part of the medium in each well.

The hybridoma, which produces the first monoclonal antibody of the present invention, is obtained by selecting a hybridoma which produces a monoclonal antibody that binds to vWF of an animal such as guinea pig, rat, and rabbit, or a monoclonal antibody that inhibits BIPA or RIPA of platelet of an animal as described above, in accordance with an enzyme immunoassay method such as an ELISA (Enzyme-Linked Immunosorbent Assay) method. The hybridoma, which produces the second monoclonal antibody of the present invention, is obtained by selecting a hybridoma which produces a monoclonal antibody that does not exhibit reactivity with vWF of an animal such as rabbit other than human.

After confirmation of the fact that the hybridoma for producing the objective monoclonal antibody is contained in a culture, the culture is transferred to HT medium having the same composition as that of HAT medium except that aminopterin is removed from HAT medium. The hybridoma is further cultured to perform cloning in accordance with, for example, a limiting dilution method.

Thus hybridomas AJvW-1, AJvW-2, AJvW-3, and AJvW-4 have been obtained as demonstrated in Examples described later on. All of them have been deposited on Aug. 24, 1994 in National Institute of Bioscience and Human Technology of Agency of Industrial Science and Technology of Ministry of International Trade and Industry (postal code: 305, 1-3 Higashi-1-chome, Tsukuba-shi, Ibaraki-ken, Japan) under deposition numbers of FERM P-14486, FERM P-14487, FERM P-14488, and FERM P-14489 respectively in this order, which have been transferred to international deposition based on the Budapest Treaty on Sep. 29, 1995, and deposited under deposition numbers of FERM BP-5247, FERM BP-5248, FERM BP-5249, and FERM BP-5250 respectively in this order. Among the hybridomas, AJvW-2 and AJvW-4 produce the first monoclonal antibody, and AJvW-1 and AJvW-3 produce the second monoclonal antibody.

As demonstrated in Examples described later on, the monoclonal antibodies produced by AJvW-1 and AJvW-3 belong to the subclass IgG2a isotype, the monoclonal antibody produced by AJvW-2 belongs to the subclass IgG1, and the monoclonal antibody produced by AJvW-4 belongs to the subclass IgG2b. NMC-4 belongs to IgG1 as having been hitherto reported.

The monoclonal antibody of the present invention is obtained by culturing, in an appropriate medium or in mouse ascitic fluid, the hybridoma obtained as described above or a variant selected by cloning the hybridoma in accordance with the limiting dilution method, for example, a variant of the hybridoma having high antibody productivity. Alternatively, the monoclonal antibody of the present invention is also obtained by isolating a gene concerning antibody production from the obtained hybridoma, incorporating the gene into an expression vector, introducing an obtained vector into a microorganism such as *Escherichia coli*, and cultivating an obtained antibody-producing microorganism. The hybridoma includes AJvW-1, AJvW-2, AJvW-3, AJvW-4 described above, and variants thereof.

The medium for culturing the hybridoma includes, for example, a medium based on DMEM medium and further containing fetal bovine serum, L-glutamine, glucose, sodium pyruvate, 2-mercaptoethanol, and an antibiotic (for example, penicillin G, streptomycin, and gentamicin). The hybridoma of the present invention is usually cultured in the medium at 37° C. for 2 to 4 days with a gas phase comprising 5% carbon dioxide and 95% air. Alternatively, the hybridoma is cultured for about 10 to 15 days in an abdominal cavity of BALB/c mouse pretreated with 2,6,10,14-tetramethylpentadecane (for example, Pristane (trade name) produced by Sigma). Thus the monoclonal antibody is produced in an amount capable of being subjected to purification.

The monoclonal antibody thus produced can be separated and purified in accordance with an ordinary method adopted for isolation and purification of proteins from culture supernatant or ascitic fluid. Such a method includes, for example, centrifugation, dialysis, salting out based on the use of ammonium sulfate, and column chromatography based on the use of, for example, DEAE-cellulose, hydroxyapatite, protein-A agarose, and protein-G agarose.

<3> Antithrombotic Agent of the Present Invention

The antithrombotic agent of the present invention contains, as an active ingredient, the monoclonal antibody which has reactivity with human von Willebrand factor, which has action to inhibit RIPA (ristocetin-induced platelet aggregation), BIPA (botrocetin-induced platelet aggregation), and SIPA (shear stress-induced platelet aggregation) of human platelet, and which does not express bleeding action in an medicinally effective dose to exhibit antithrombotic action. Such a monoclonal antibody specifically includes the first monoclonal antibody and the second monoclonal antibody of the present invention. As described above, it is expected that the monoclonal antibody, which has action to inhibit binding between the first and second monoclonal antibodies and vWF factor when the monoclonal antibody is allowed to co-exist with the first and second monoclonal antibodies, also has the same action as those of the first and second monoclonal antibodies, and it is used as an active ingredient of the antithrombotic agent of the present invention.

When the monoclonal antibody originating from mouse is applied as an antithrombotic agent to human, it is desirable that the monoclonal antibody is modified into one of the human type, because of problems of antigenicity and half-life in blood. Variable regions of the antibody can be converted into those of the human type without losing the reaction specificity in accordance with methods described by Jones et al. (*Nature*, vol. 321, p. 522, 1986) and Queen et al. (*Proc. Natl. Acad. Sci. USA*, vol. 86, p. 10029, 1989). Recently, the repertoire cloning method described by Winter et al. and Lerner et al. is also available (*J. Mol. Biol.*, vol. 222, p. 581, 1991; *Proc. Natl. Acad. Sci. USA*, vol. 88, p. 2432, 1991).

Fragments F(ab')$_2$, Fab', and Fab, which can be obtained by digesting the foregoing monoclonal antibody with a proteolytic enzyme such as trypsin, papain, and pepsin, followed by purification, can be also used as the antithrombotic agent provided that the fragments have properties equivalent to those of the foregoing monoclonal antibody.

The type or form of the antithrombotic agent of the present invention includes, for example, injection, sublingual tablet, endermic poultice, tablet or pill, capsule, granule, syrup, suppository, ointment, and instillation. Among them, injection, sublingual tablet, and endermic poultice are preferred. Depending on the type of the agent, the antithrombotic agent may be blended with pharmaceutically allowable excipients, for example, lactose, potato starch, calcium carbonate, and sodium alginate. In the case of injection, those used as a solvent include, for example, water for injection, physiological saline, and Ringer's solution. The solvent may be added with a dispersing agent. Further, an antithrombotic component other than the anti-vWF monoclonal antibodies may be used together.

The dose of administration of the antithrombotic agent of the present invention differs depending on, for example, the age and the condition of a patient. However, in general, in the case of intravenous administration, a predetermined effect can be expected by using the antithrombotic agent of the present invention preferably in a range of 0.1 µg/kg to 1000 mg/kg, more preferably 1 µg/kg to 100 mg/kg per one day for an adult, as represented by amount of the monoclonal antibody to serve as an active ingredient.

The antithrombotic agent of the present invention may be applied to general applications concerning antithrombotic agents. Namely, the antithrombotic agent of the present invention may be applied to prevent or treat diseases relevant to platelet adhesion and aggregation. Specifically, for example, the antithrombotic agent of the present invention is effective in the treatment of transient cerebral ischemic attack, unstable angina pectoris, cerebral infarction, myocardial infarction, and peripheral arterial occlusive disease, it is effective in the prevention of reocclusion after PTCA and occlusion of coronary artery by-pass graft, and it is effective in the treatment of coronary artery valve replacement and essential thrombocythemia.

BRIEF DESCRIPTION OF THE DRAWINGS

FIG. 17 shows effects of the respective monoclonal antibodies on binding of biotinylated AJvW-2 to immobilized vWF.

FIG. 18 shows effects of the respective monoclonal antibodies on binding of biotinylated AJvW-3 to immobilized vWF.

BEST MODE FOR CARRYING OUT THE INVENTION

Figure 1:
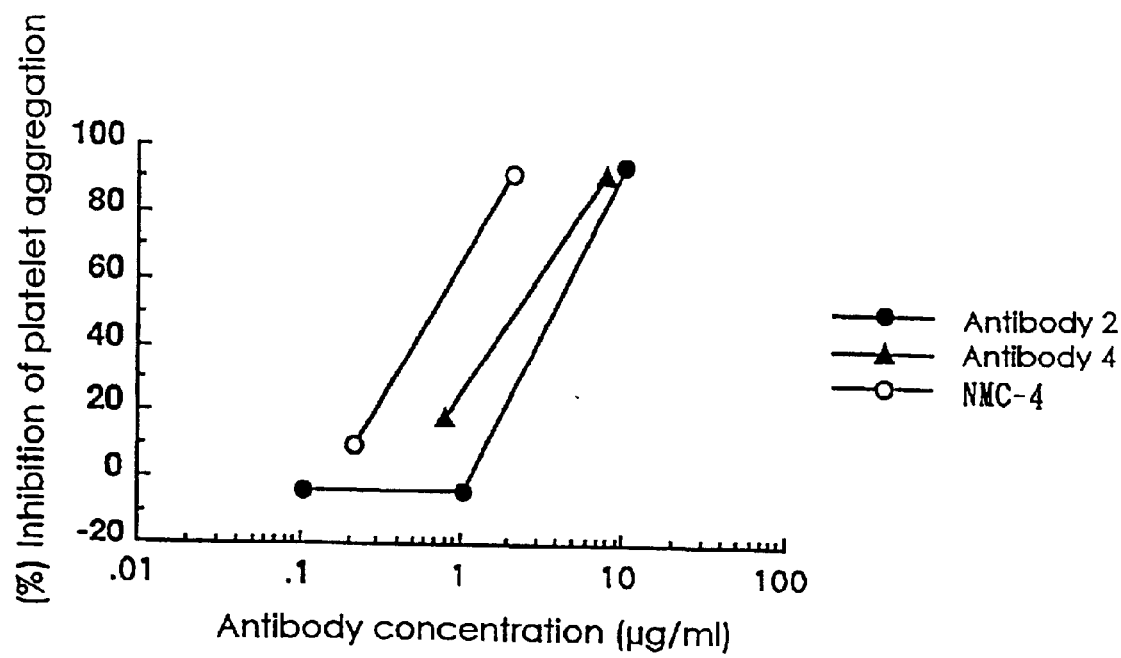
FIG. 1 shows inhibitory activities of Antibody 2 and Antibody 4 concerning Examples of the present invention and NMC-4 as a comparative control, measured in RIPA based on the use of human PRP.

The present invention will be more specifically explained below making reference to Examples. However, the present invention is not limited to Examples described below.

EXAMPLES

<1> Preparation of Monoclonal Antibodies (1) Immunosensitization and Cell Fusion Purified human vWF was mixed with an equal amount of an adjuvant (MPL+TDM EMULSION: trade name of RIBI), and an obtained mixture was subcutaneously administrated to Balb/c male mice (8 weeks old upon the start of immunization) in an amount corresponding to an amount of vWF of 100 µg per 1 mouse (priming immunization). After 21 days, immunization was performed by subcutaneous administration in the same manner as described above (booster immunization). After 19 days or 30 days from the booster, the mice were administrated through their tail veins with 200 µl of a preparation obtained by diluting human vWF with PBS (phosphate-buffered physiological saline, produced by Nissui) to have a concentration of 250 µg/ml (final immunization).

Spleens were excised from the mice after 3 days from the final immunization, and they were separated into single cells. Subsequently, the spleen cells were washed with DMEM medium. On the other hand, mouse myeloma cells Sp2/0-Ag14 in the logarithmic growth phase were collected, and they were washed with DMEM medium. The spleen cells and the mouse myeloma cells were sufficiently mixed in a plastic tube in a ratio of numbers of the cells of 10:1, followed by addition of 50% (w/v) polyethylene glycol (produced by Boehringer Mannheim, average molecular weight: 4000) to perform cell fusion at 37° C. for 7 minutes.

A supernatant solution was removed by means of centrifugation, and a residue is added with HAT medium (DMEM medium containing 10% fetal bovine serum added with hypoxanthine, aminopterin, and thymidine). The residue was suspended so that the concentration of the spleen cells was $5 \times 10^6$ cells/ml. This cell suspension was dispensed and poured into 96-well plastic plates so that one well contained 100 µl of the suspension, followed by cultivation at 37° C. in 5% carbon dioxide. HAT medium was supplemented in an amount of 50 µl/well on 2nd and 5th days. After that, half volume of the medium was exchanged every 3 or 4 days in conformity with proliferation of hybridomas.

(2) Screening and Cloning of Hybridomas

Hybridomas, which produced the monoclonal antibody of the present invention, were screened by using, as an index, the inhibitory activity of the monoclonal antibody on the physiological activity possessed by vWF. A part of the medium in each of the wells after completion of proliferation of hybridomas was sampled, for which the inhibitory activities on RIPA and BIPA were measured. Hybridoma clones, which strongly inhibited the both reactions, were selected.

Hybridomas, which produced monoclonal antibodies exhibiting reactivity with vWF's of guinea pig, rabbit, and rat, were selected from the selected clones. The obtained hybridomas were transferred to HT medium which was the same as HAT medium except that aminopterin was removed from HAT medium, and they were further cultured. Cloning was performed twice in accordance with the limiting dilution method. Thus stable hybridomas were obtained. Finally obtained two hybridomas were designated as AJvW-2 and AJvW-4.

On the other hand, hybridomas, which produced monoclonal antibodies exhibiting no reactivity with VWF's of guinea pig, rabbit, and rat, were selected from the clones which strongly inhibited the reactions of RIPA and BIPA described above. The obtained hybridomas were transferred to HT medium which was the same as HAT medium except that aminopterin was removed from HAT medium, and they were further cultured. Cloning was performed twice in accordance with the limiting dilution method. Thus stable hybridomas were obtained. Finally obtained two hybridomas were designated as AJvW-1 and AJvW-3.

AJvW-2 and AJvW-4 produced the first monoclonal antibody of the present invention, and AJvW-1 and AJvW-3 produced the second monoclonal antibody of the present invention.

<2> Production and Purification of Monoclonal Antibodies (1) Production of Monoclonal Antibodies 2,6,10,14-Tetramethylpentadecane (trade name: Pristane, produced by Sigma, 0.5 ml) was intraperitoneally injected into Balb/c female mice which were 6 to 8 weeks old from the birth. After 10 to 20 days, cells of AJvW-1, AJvW-2, AJvW-3, or AJvW-4 ($1 \times 10^6$ to $10^7$ cells) were suspended in PBS, and they were intraperitoneally inoculated into the mice. After 7 to 10 days, the mice were sacrificed and subjected to an abdominal operation, from which produced ascitic fluid was collected. The ascitic fluid was centrifuged to remove insoluble matters, and a supernatant was recovered and stored at −20° C.

(2) Purification of Monoclonal Antibodies

IgG was purified from the ascitic fluid supernatant described above by using Hi-Trap Protein-A antibody purification kit (trade name, produced by Pharmacia). Namely, the ascitic fluid (2 ml) was added with Solution A (1.5 M glycine, 3 M NaCl, pH 8.9, 8 ml), and filtrated with a filter for filtration having a pore size of 45 µm (produced by Millipore). After that, an obtained filtrate was applied to a column (column volume: 1 ml) charged with Protein Sepharose HP (produced by Pharmacia) sufficiently equilibrated with Solution A, and the column was washed with Solution A in an amount of 10-fold column volume. Subsequently, an IgG fraction was eluted with Solution B (0.1 M glycine, pH 2.8) in an amount of 10-fold column volume. The eluted IgG fraction was dialyzed against PBS, which was used as a purified sample.

The monoclonal antibodies produced by AJvW-1, AJvW2, AJvW-3, and AJvW-4 will be hereinafter referred to as "Antibody 1", "Antibody 2", "Antibody 3", and "Antibody 4" respectively in this order.

NMC-4 was purified from mouse ascitic fluid containing NMC-4 in the same manner as described above in order to obtain a sample to be used as a comparative control.

<3> Determination of Subclasses of Monoclonal Antibodies

The monoclonal antibodies of the present invention were determined for their IgG subclasses by using the purified antibodies obtained in the foregoing item<2>, by means of a commercially available subclass-determining kit (trade name: Mono Ab-ID EIA Kit A, produced by Zymed). This method is based on the ELISA method. As a result, all of Antibody 1, Antibody 2, Antibody 3, and Antibody 4 belonged to the class of IgG. It was determined that the subclass of Antibody 1 and Antibody 3 was IgG2a isotype, the subclass of Antibody 2 was IgG1 isotype, and the subclass of Antibody 4 was IgG2b isotype. NMC-4 belonged to IgG1, as having been hitherto reported.

<4> Inhibitory Activities of Monoclonal Antibodies of the Present Invention on Platelet Aggregation (1) Inhibitory Activities on RIPA Blood obtained from a normal human donor was mixed with 3.8% sodium citrate in a ratio of 9:1, which was then centrifuged at 1100 rpm for 10 minutes to prepare platelet rich plasma (PRP). PRP ($3 \times 10^8$ platelets/ml, 225 µl) was reacted at 37° C. for 3 minutes with the monoclonal antibody (2 µl) at various concentrations. After that, ristocetin (produced by Sigma) was added thereto to give a final concentration of 1.5 mg/ml. Platelet aggregation was monitored at 37° C. for 10 minutes by using an apparatus for measuring platelet aggregation ability (trade name: HEMATRCER, produced by Niko Bioscience). The extent of platelet aggregation was expressed by change in optical transmittance. The inhibitory activity on platelet aggregation was determined by using, as a control, the maximal aggregation obtained by adding DMEM or the buffer for dissolving the sample.

Figure 2:
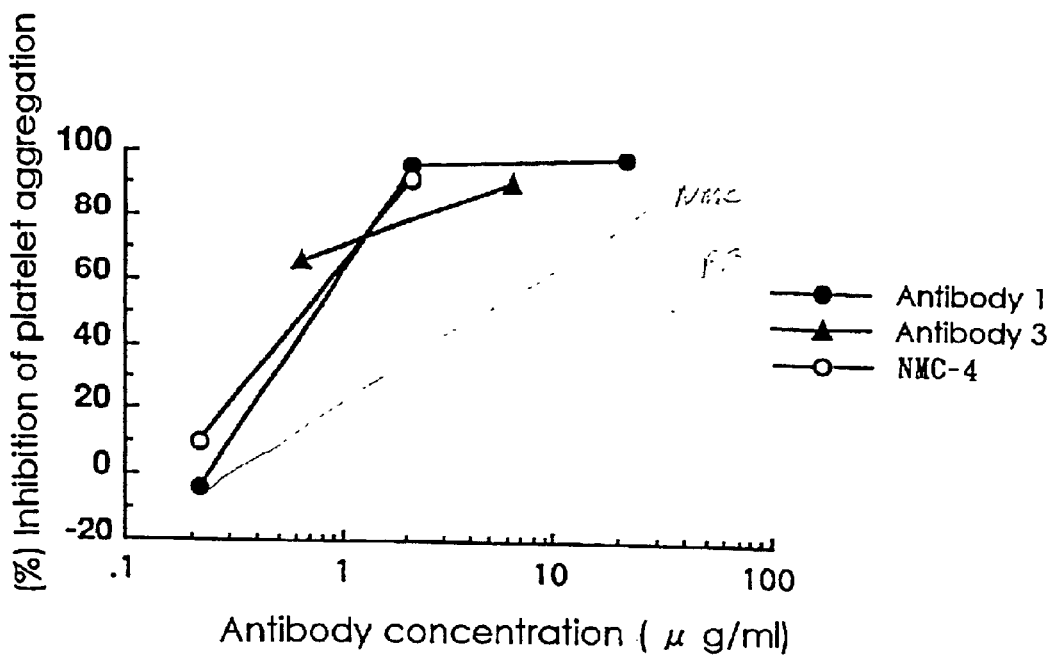
FIG. 2 shows inhibitory activities of Antibody 1 and Antibody 3 concerning Examples of the present invention and NMC-4 as a comparative control, measured in RIPA based on the use of human PRP.

Results are shown in FIG. 1 (Antibodies 2, 4) and FIG. 2 (Antibodies 1, 3). Any of Antibody 1, Antibody 2, Antibody 3, Antibody 4, and NMC-4 inhibited human RIPA in a dose-dependent manner. Values of $IC_{50}$ were 0.8 μg/ml for Antibody 1, 3.5 μg/ml for Antibody 2, 1.0 μg/ml for Antibody 3, 2.0 μg/ml for Antibody 4, and 0.7 μg/ml for NMC-4.

Figure 3:
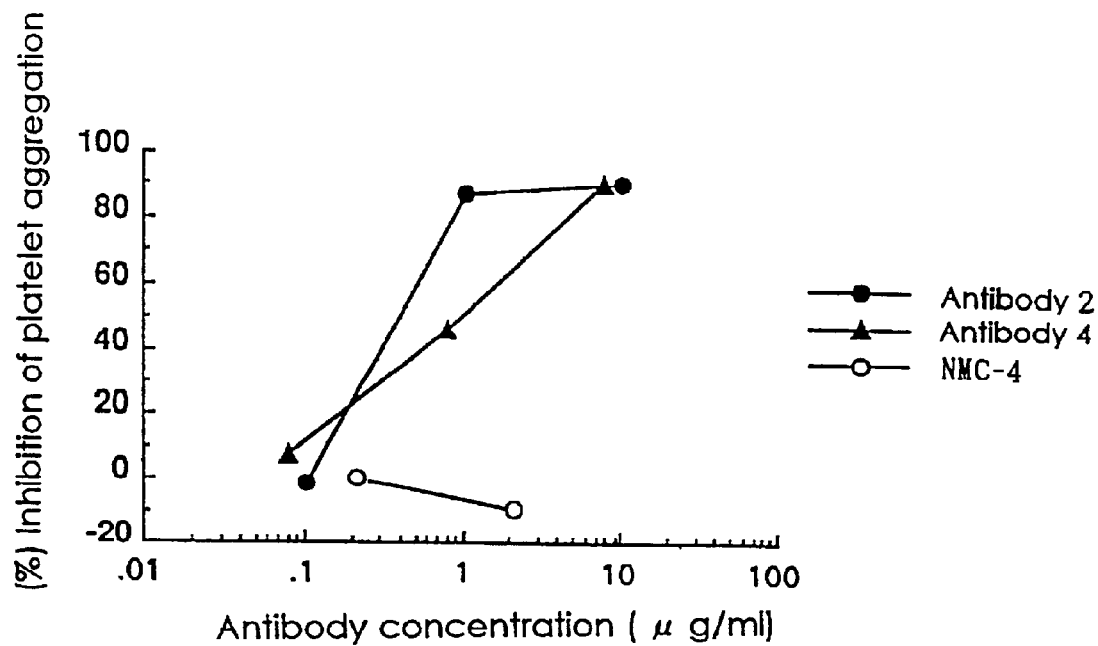
FIG. 3 shows inhibitory activities of Antibody 2, Antibody 4, and NMC-4, measured in RIPA based on the use of guinea pig PRP.

PRP of guinea pig was prepared in the same manner as described above, to which ristocetin was added to give a final concentration of 1.75 mg/ml, and measurement was performed in the same manner as described above. Antibody 1 (final concentration: 80 μg/ml), Antibody 3 (final concentration: 80 μg/ml), and NMC-4 (final concentration: 27 μg/ml) did not inhibit RIPA of guinea pig at all, while Antibody 2 and Antibody 4 inhibited guinea pig RIPA in a dose-dependent manner (FIG. 3). Values of $IC_{50}$ were 0.4 μg/ml for Antibody 2 and 1 μg/ml for Antibody 4.

(2) Inhibiting Activities on BIPA

Before measurement of BIPA, a snake venom, i.e., botrocetin was purified from a crude venom preparation (produced by Sigma) obtained from Bothorops jararaca. Namely, 1 g of the crude venom preparation was dissolved in 20 mM Tris-HCl buffer (pH 7.4) containing 0.15 M NaCl, and insoluble matters were removed by centrifugation at 3000 rpm. An obtained supernatant was subjected to gel filtration by using Sephadex G-75 (5×90 cm, produced by Pharmacia). Fractions corresponding to a range of elution volume of 480 to 570 ml were collected, and an obtained solution was concentrated into a volume of 20 ml by using an ultrafiltration concentrating apparatus (DIAFLO YM-10, produced by Amicon). After that, the concentrated solution was applied to an ion exchange column based on the use of DEAE-TOYOPEARL-650M (1.6×32 cm, produced by Pharmacia), followed by elution by applying a concentration gradient of 0 to 0.3 M NaCl. Fractions eluted between 600 and 640 minutes were collected, and an obtained solution was concentrated into a volume of 4 ml in the same manner as described above. After that, the concentrated solution was applied to a gel filtration column (Sephadex G-75, 2.6×90 cm, produced by Pharmacia) by using, as a solvent, 20 mM Tris-HCl buffer (pH 7.4) containing 0.15 M NaCl. Fractions having strong platelet-aggregating activities were recovered, and a combined solution was used as a purified sample.

Figure 4:
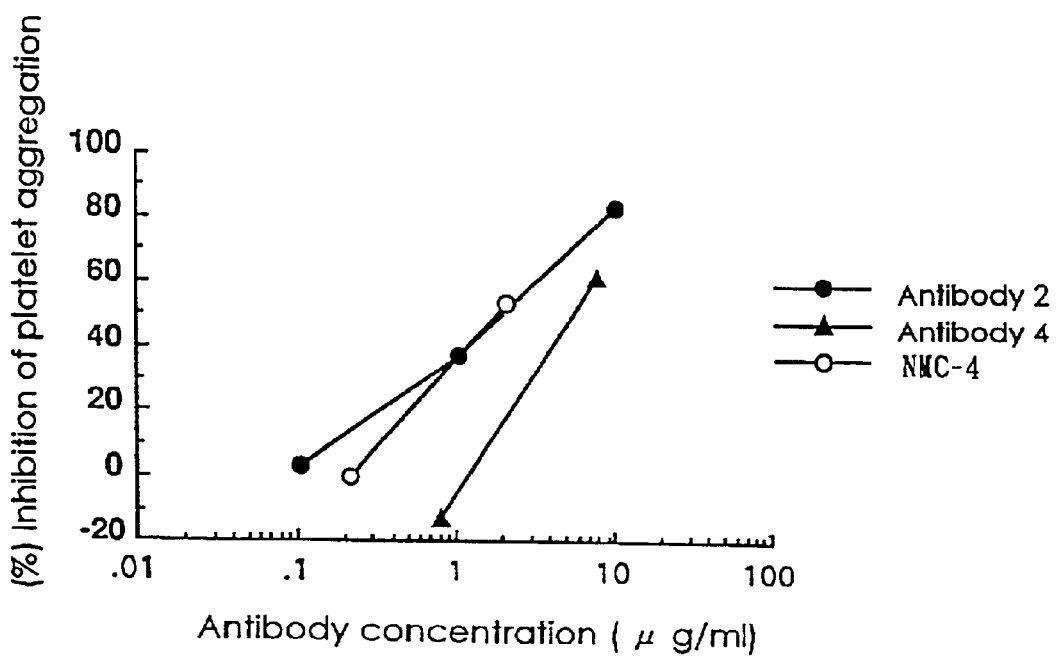
FIG. 4 shows inhibitory activities of Antibody 2, Antibody 4, and NMC-4, measured in BIPA based on the use of human PRP.
Figure 5:
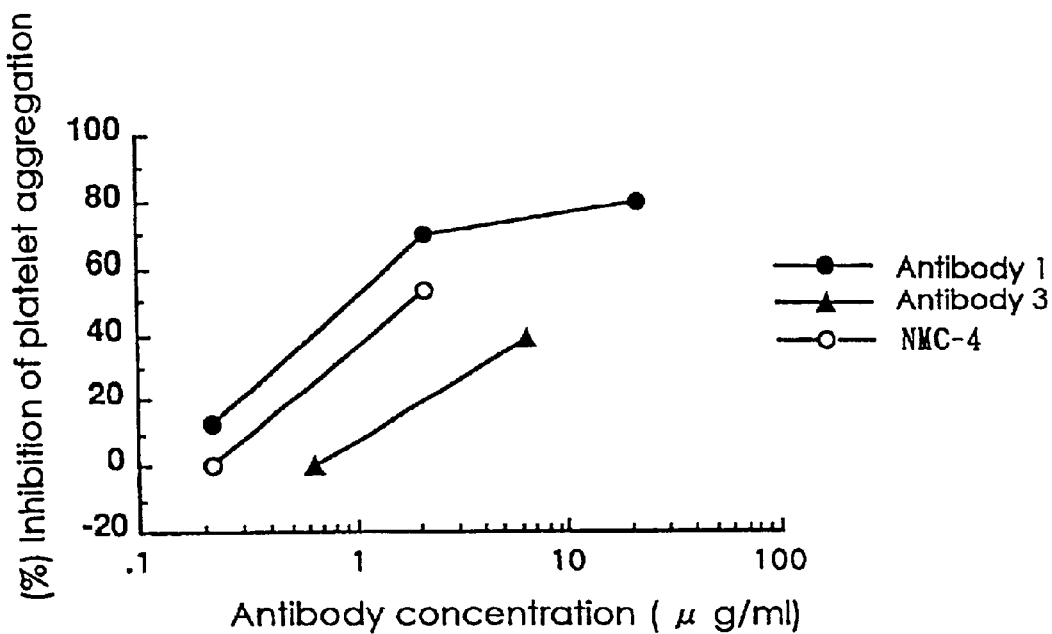
FIG. 5 shows inhibitory activities of Antibody 1, Antibody 3, and NMC-4, measured in BIPA based on the use of human PRP.

Human PRP ($3 \times 10^8$ platelets/ml, 225 μl) was reacted at 37° C. for 3 minutes with the monoclonal antibody (2 μl) at respective concentrations. After that, the reaction mixture was added with botrocetin having been obtained as described above to give a final concentration of 5 μg/ml, and platelet aggregation was measured in accordance with the same method as that described in the foregoing item (1). Results are shown in FIG. 4 (Antibodies 2, 4) and FIG. 5 (Antibodies 1, 3). Any of Antibody 1, Antibody 2, Antibody 3, Antibody 4, and NMC-4 inhibited BIPA in a dose-dependent manner. $IC_{50}$ values were 0.8 μg/ml for Antibody 1, 2.0 μg/ml for Antibody 2, 1.0 μg/ml for Antibody 3, 5.6 μg/ml for Antibody 4, and 2.0 μg/ml for NMC-4.

Figure 6:
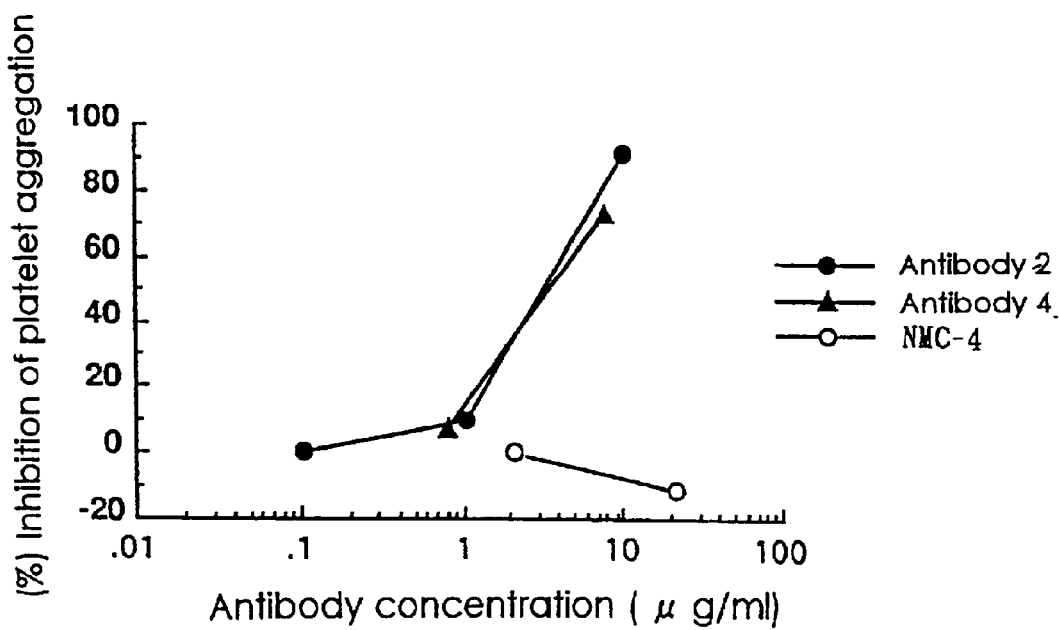
FIG. 6 shows inhibitory activities of Antibody 2, Antibody 4, and NMC-4, measured in BIPA based on the use of guinea pig PRP.

Guinea pig PRP was prepared in the same manner as described above, to which botrocetin was added to give a final concentration of 2 μg/ml, and measurement was performed in the same manner as described above. Antibody 1 (final concentration: 80 μg/ml), Antibody 3 (final concentration: 80 μg/ml), and NMC-4 (final concentration: 27 μg/ml) did not inhibit BIPA at all, while Antibody 2 and Antibody 4 inhibited BIPA in a dose-dependent manner (FIG. 6). $IC_{50}$ values were 3.1 μg/ml for Antibody 2 and 3.5 μg/ml for Antibody 4.

Figure 7:
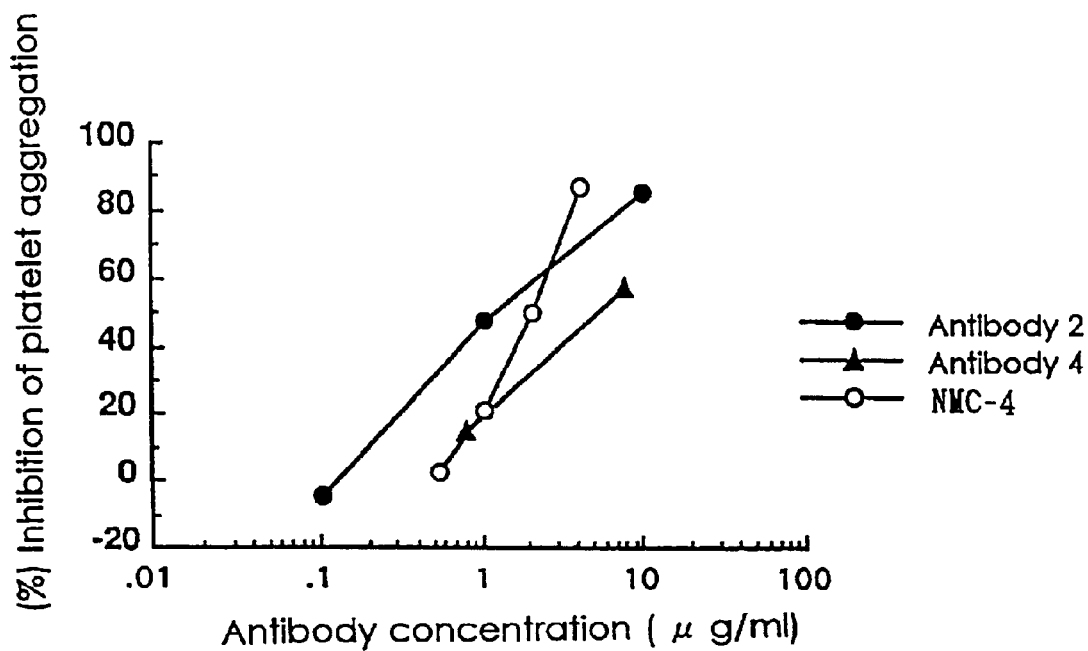
FIG. 7 shows inhibitory activities of Antibody 2, Antibody 4, and NMC-4, measured in BIPA based on the use of rat PRP.

PRP was prepared by centrifuging citrated blood of rat at 1300 rpm for 10 minutes. Botrocetin was added to PRP ($5 \times 10^6$ platelets/ml) to give a final concentration of 0.08 μg/ml, and measurement was performed in the same manner as described above. Antibody 1 (final concentration: 80 μg/ml) and Antibody 3 (final concentration: 80 μg/ml) did not inhibit BIPA of rat at all, while Antibody 2, Antibody 4, and NMC-4 inhibited BIPA in a dose-dependent manner (FIG. 7). Values of $IC_{50}$ were 1.2 μg/ml for Antibody 2, 5.0 μg/ml for Antibody 4, and 2.2 μg/ml for NMC-4.

Figure 8:
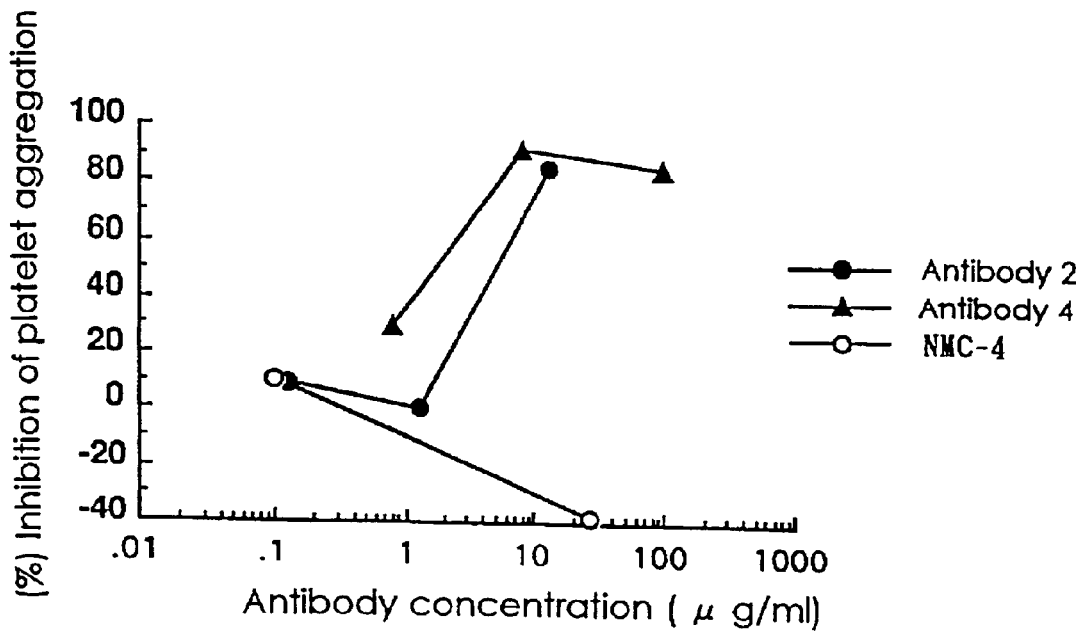
FIG. 8 shows inhibitory activities of Antibody 2, Antibody 4, and NMC-4, measured in BIPA based on the use of rabbit PRP.
Figure 9:
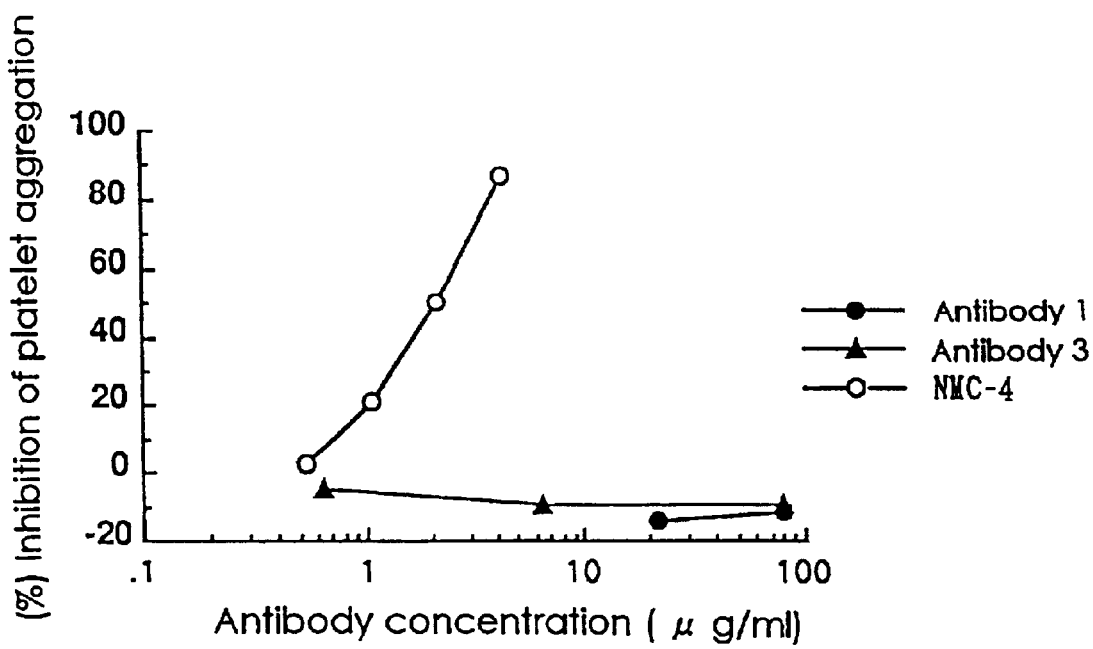
FIG. 9 shows inhibitory activities of Antibody 1, Antibody 3, and NMC-4, measured in BIPA based on the use of rabbit PRP.

PRP was prepared by centrifuging citrated blood of rabbit at 1200 rpm for 10 minutes. Botrocetin was added to PRP ($3 \times 10^8$ platelets/ml) to give a final concentration of 0.075 μg/ml, and measurement was performed in the same manner as described above. Results are shown in FIG. 8 (Antibodies 2, 4) and FIG. 9 (Antibodies 1, 3). Antibody 1 (final concentration: 80 μg/ml), Antibody 3 (final concentration: 80 μg/ml), and NMC-4 (final concentration: 27 μg/ml) did not inhibit rabbit BIPA at all, while Antibody 2 and Antibody 4 inhibited BIPA in a dose-dependent manner. $IC_{50}$ values were 5.0 μg/ml for Antibody 2 and 1.8 μg/ml for Antibody 4.

(3) Inhibitory Activities on SIPA

Human PRP ($2.5 \times 10^8$ platelets/ml, 360 μl) was reacted at room temperature for 10 minutes with the monoclonal antibody (40 μl) at respective concentrations. After that, platelet aggregation induced by shear stress was measured by using an apparatus for measuring cell function (produced by Toray). Namely, the reaction mixture was applied with constant shear of 6 dyne/cm$^2$ during a period of 0 to 15 seconds, low-shear gradient of 6→12 dyne/cm$^2$ during a period of 15 to 105 seconds, high-shear gradient of 12→108 dyne/cm$^2$ during a period of 105 to 225 seconds, and constant shear of 108 dyne/cm$^2$ during a period up to 350 seconds. The extent of platelet aggregation activity was represented by change in optical transmittance. The inhibitory activity on platelet aggregation was determined by using, as a control, the maximal aggregation obtained by adding DMEM or the buffer for dissolving the sample.

Figure 10:
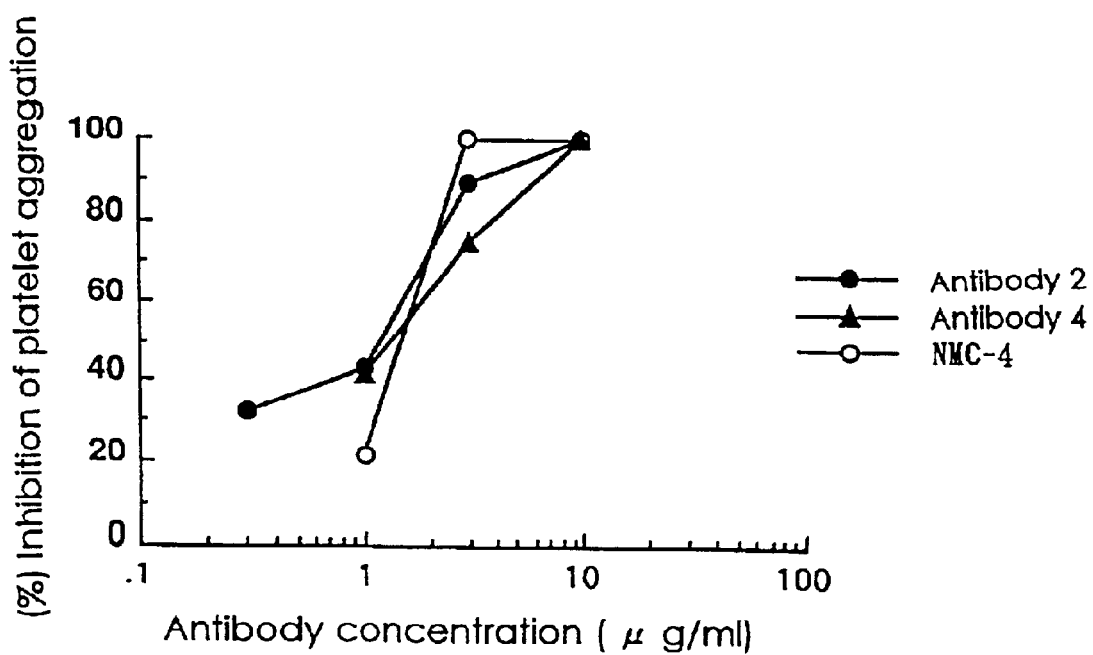
FIG. 10 shows inhibitory activities of Antibody 2, Antibody 4, and NMC-4, measured in SIPA based on the use of human PRP.
Figure 11:
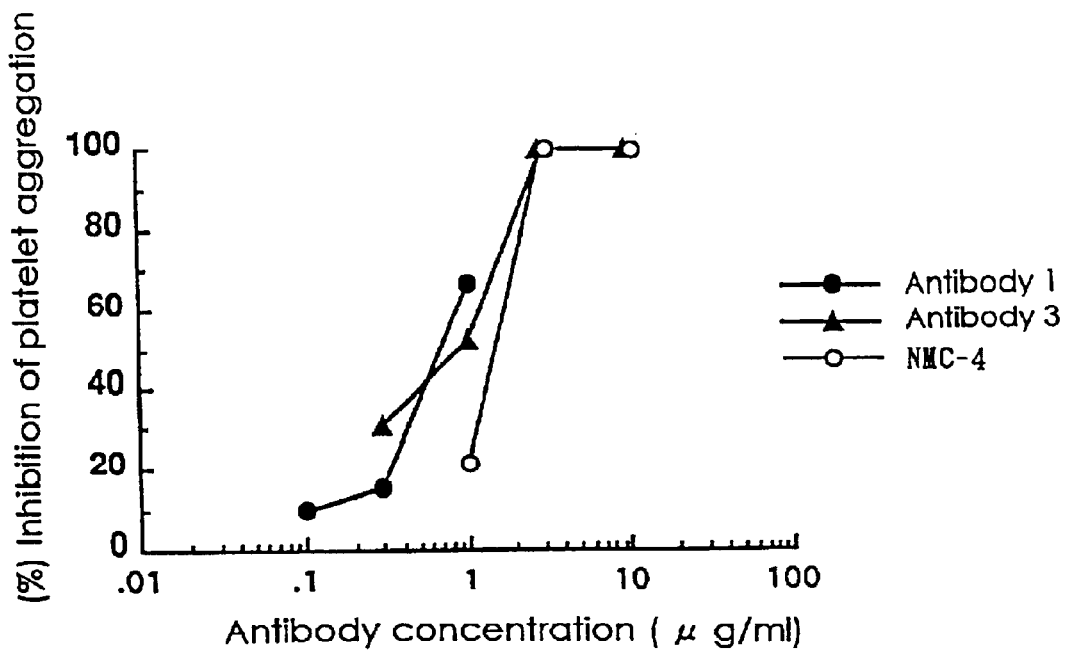
FIG. 11 shows inhibitory activities of Antibody 1, Antibody 3, and NMC-4, measured in SIPA based on the use human PRP.

Results are shown in FIG. 10 (Antibodies 2, 4) and FIG. 11 (Antibodies 1, 3). Any of Antibody 1, Antibody 2, Antibody 3, Antibody 4, and NMC-4 inhibited SIPA of human in a dose-dependent manner. $IC_{50}$ values were 0.7 μg/ml for Antibody 1, 1.1 μg/ml for Antibody 2, 0.9 μg/ml for Antibody 3, 1.5 μg/ml for Antibody 4, and 1.5 μg/ml for NMC-4.

<5> Affinity of Monoclonal Antibodies of the Present Invention to Human vWF (1) $^{125}$I-labeling for Human vWF Iodogen (produced by Pierce, 1 mg/ml) and a dichloromethane solution (1 ml) were added to a polypropylene tube from which the solvent was removed by using nitrogen stream. A solution of human vWF (0.43 mg/ml) was poured into the polypropylene tube to which a solution of Na$^{125}$I (15.9 MBq, 8.6 μl) was added to perform a reaction at room temperature for 2 minutes. After the reaction, the reaction solution was applied to a PD10 column (produced by Pharmacia) having been previously blocked with a TBS solution (Tris-buffered saline) containing 2 ml of 10% BSA (bovine serum albumin) and washed with 100 ml of TBS.

Elution was performed with TBS. The eluted solution was fractionated into fractions each having a volume of 500 μl. An aliquot (2 μl) of each of the eluted fractions was measured for its radioactivity by using a γ-counter (counting time: 1 minute). Fractions having high counted values were collected, and a combined fraction (1 ml) was designated as a solution of $^{125}$I-labeled human vWF ($^{125}$I-vWF) (0.3 mg/ml human vWF, 220630 cpm/μl).

(2) Preparation of Immobilized Platelets

Human PRP collected in the same manner as described in the foregoing item<4> (1) was added and mixed with an equal volume of 2% paraformaldehyde solution, followed by being left to stand at 4° C. overnight. On the next day, immobilized platelets were recovered and washed three times with PBS by means of centrifugation operation. After that, the immobilized platelets were resuspended in PBS having a volume equal to that for PRP upon the collection, and an obtained suspension was used as an immobilized platelet suspension.

(3) Action of Monoclonal Antibodies of the Present Invention on Platelet-binding Property of vWF The immobilized platelet suspension, a solution of the antibody at various concentrations, and a ristocetin solution or a botrocetin solution were dispensed and poured into 96-well filtration filter plate having been previously blocked with PBS containing 1% BSA, to which the $^{125}$I-vWF solution was added, followed by being left to stand at room temperature for 30 minutes. After the plate was left to stand, $^{125}$I-vWF not bound to the immobilized platelets was removed by filtration by means of suction, and the filter was washed with PBS containing 0.05% Tween-20. $^{125}$I remaining on the filter was measured by using a γ-counter (adding up time: 1 minute) to determine the amount of binding of human vWF to the immobilized platelets. The ratio of the binding amount of human vWF to the platelets in the presence of the antibody to the binding amount of human vWF to the platelets in the absence of the antibody was designated as binding ratio (%).

Figure 12:
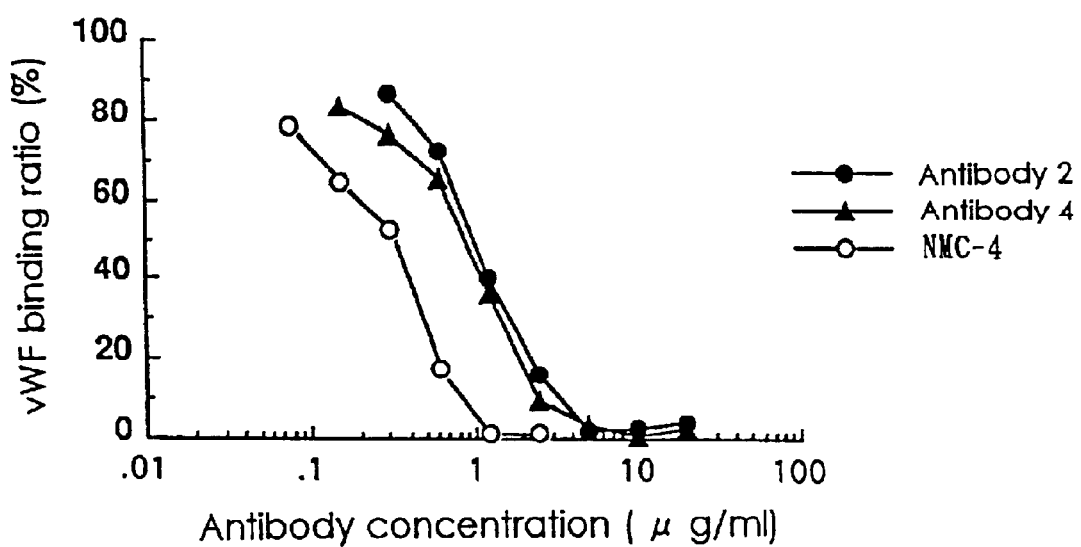
FIG. 12 shows influences of Antibody 2, Antibody 4, and NMC-4, on binding of vWF to immobilized human platelet (in the presence of ristocetin).
Figure 13:
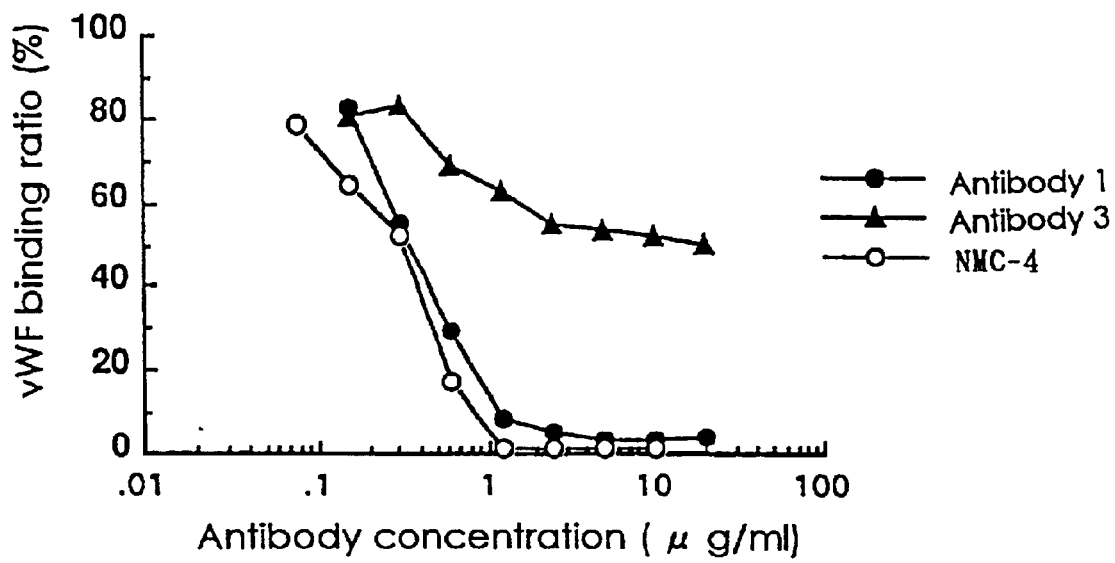
FIG. 13 shows influences of Antibody 1, Antibody 3, and NMC-4, on binding of vWF to immobilized human platelet (in the presence of ristocetin).
Figure 14:
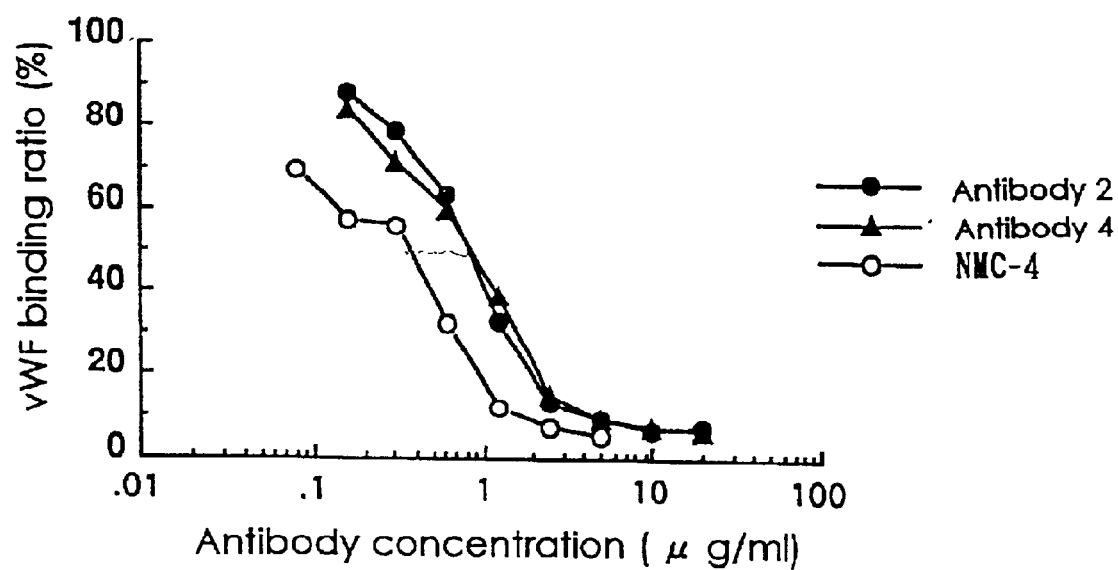
FIG. 14 shows influences of Antibody 2, Antibody 4, and NMC-4, on binding of vWF to immobilized human platelet (in the presence of botrocetin).
Figure 15:
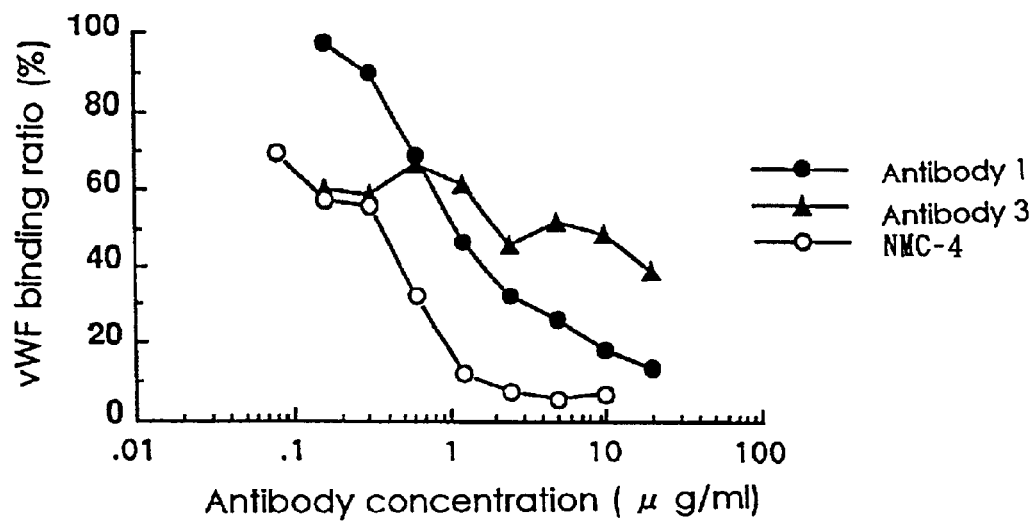
FIG. 15 shows influences of Antibody 1, Antibody 3, and NMC-4, on binding of vWF to immobilized human platelet (in the presence of botrocetin).
Figure 16:
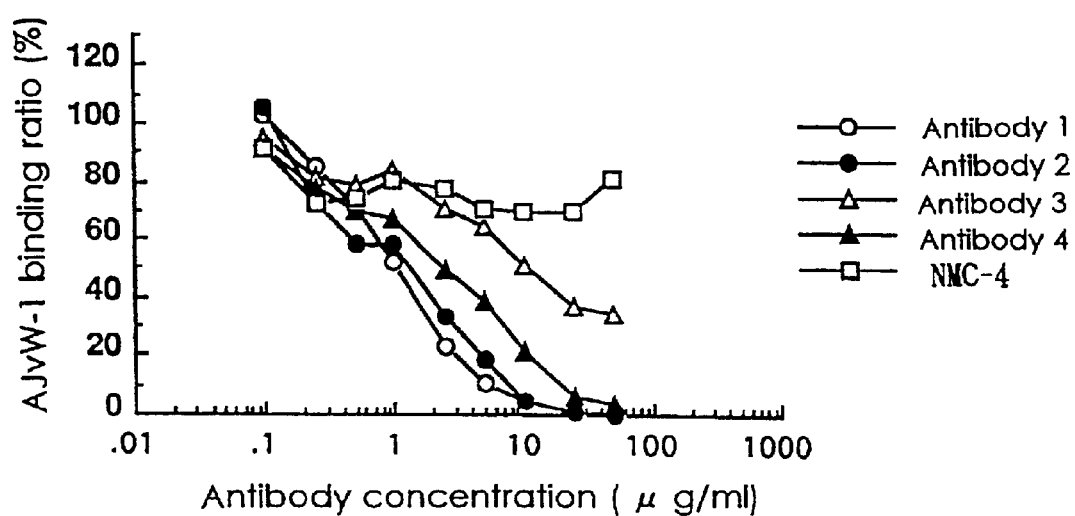
FIG. 16 shows effects of the respective monoclonal antibodies on binding of biotinylated AJvW-1 to immobilized vWF.
Figure 19:
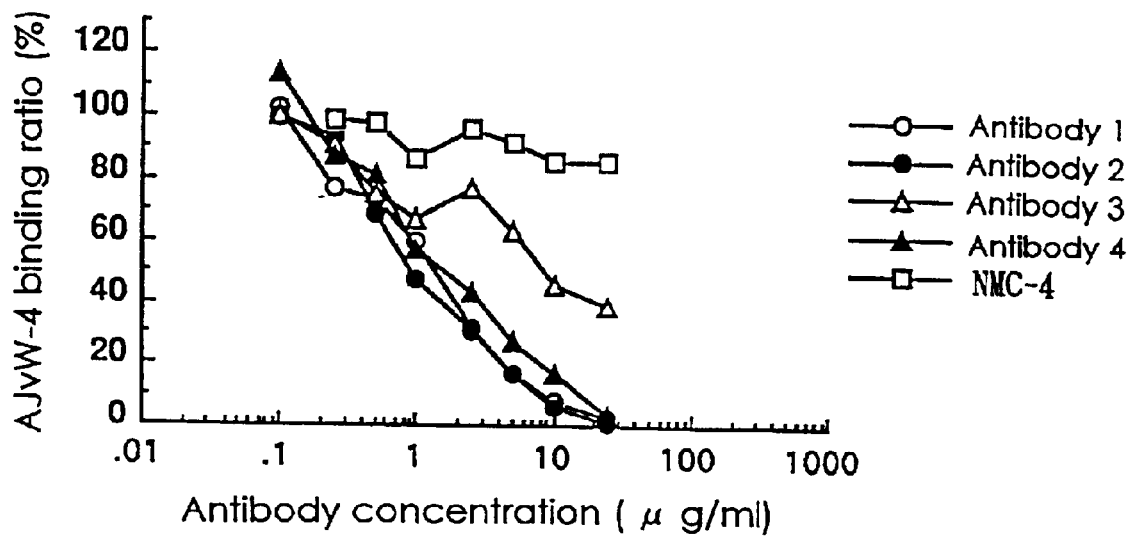
FIG. 19 shows effects of the respective monoclonal antibodies on binding of biotinylated AJvW-4 to immobilized vWF.
Figure 20:
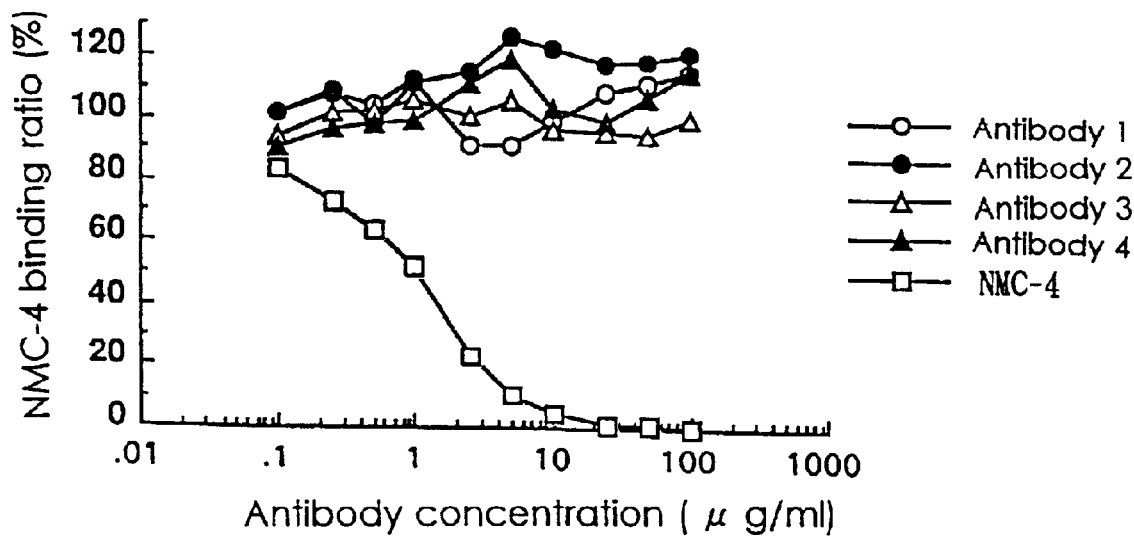
FIG. 20 shows effects of the respective monoclonal antibodies on binding of biotinylated NMC-4 to immobilized vWF.

Results obtained in the presence of ristocetin are shown in FIG. 12 (Antibodies 2, 4) and FIG. 13 (Antibodies 1, 3). Results obtained in the presence of botrocetin are shown in FIG. 14 (Antibodies 2, 4) and FIG. 15 (Antibodies 1, 3). All of Antibody 1, Antibody 2, Antibody 3, Antibody 4, and NMC-4 inhibited the ristocetin-dependent binding and the botrocetin-dependent binding of vWF to the platelets in a dose-dependent manner. $IC_{50}$ values in the ristocetin-dependent reaction were 0.37 μg/ml for Antibody 1, 1.1 μg/ml for Antibody 2, 20.0 μg/ml for Antibody 3, 0.95 μg/ml for Antibody 4, and 0.35 μg/ml for NMC-4. $IC_{50}$ values in the botrocetin-dependent reaction were 1.2 μg/ml for Antibody 1, 0.9 μg/ml for Antibody 2, 2.1 μg/ml for Antibody 3, 0.9 μg/ml for Antibody 4, and 0.3 μg/ml for NMC-4.

<6> Comparison of Epitopes of Antibody 1, Antibody 2, Antibody 3, and Antibody 4 with epitope of NMC-4

In order to compare epitopes of Antibody 1, Antibody 2, Antibody 3, and Antibody 4 with an epitope of NMC-4, inhibiting effects of Antibody 1, Antibody 2, Antibody 3, and Antibody 4 on the binding of NMC-4 to immobilized human vWF were investigated.

Purified Antibody 1, Antibody 2, Antibody 3, Antibody 4, and NMC-4 were biotinylated by using Biotinylation kit (trade name of Amersham) to prepare respective samples of Biotinylated Antibody 1, Biotinylated Antibody 2, Biotinylated Antibody 3, Biotinylated Antibody 4, and Biotinylated NMC-4. Namely, a solution of each of the monoclonal antibodies dialyzed against PBS solution was added with a solution of biotin-spacer arm-N-hydroxysuccinimide ester to perform a reaction at room temperature for 1 hour, followed by purification by using a column of Sephadex G25 (produced by Pharmacia).

Human vWF (5 μg/ml) dissolved in PBS solution was added in an amount of 50 μl to each of wells of E.I.A Microtitration plate (produced by Linbro/Titertek), followed by being left to stand at 4° C. overnight. Thus human vWF was immobilized. On the next day, each of the wells was washed three times with a washing solution (PBS containing 0.05% Tween 20), to which PBS solution containing 0.5% BSA was added, followed by being left to stand at room temperature for 1.5 hour. Thus portions to which no protein was adsorbed were blocked.

Each of the biotinylated antibodies was mixed with non-biotinylated Antibody 1, Antibody 2, Antibody 3, Antibody 4, or NMC-4 in an Eppendorf tube, and each of obtained solutions was added to each of the human vWF-immobilized wells described above in an amount of 50 μl to perform incubation at 37° C. for 1 hour. After washing the wells, each of the wells was added with 50 μl of a solution of streptavidin-alkaline phosphatase (produced by Amersham) diluted 500 times with 0.05 M TBS containing 0.05% Tween 20 and 1% BSA, followed by performing a reaction at 37° C. for 1 hour.

After washing the wells, each of the wells was added with 100 μl of a color-developing substrate, i.e., p-nitrophenyl phosphate (produced by Sigma), followed by being stationarily left to stand for 20 minutes. The biotinylated antibody bound to human vWF was measured on the basis of absorbance at 405 nm. Non-specific binding was measured in the presence of an excessive amount (100-fold) the non-biotinylated antibody in the same manner as described above. A value measured in the latter measurement was subtracted from a value measured in the former measurement to obtain a value which was designated as specific absorption.

Results are shown in FIGS. 16 to 20. Antibody 1, Antibody 2, Antibody 3, and Antibody 4 did not inhibit binding of Biotinylated NMC-4 to the immobilized vWF at all, while they inhibited binding of Biotinylated Antibody 1, Biotinylated Antibody 2, Biotinylated Antibody 3, and Biotinylated Antibody 4 to the immobilized vWF with each other. On the other hand, NMC-4 did not inhibit binding of Biotinylated Antibody 1, Biotinylated Antibody 2, Biotinylated Antibody 3, and Biotinylated Antibody 4 to the immobilized vWF at all. According to the foregoing results, it has been demonstrated that the epitopes for Antibody 1, Antibody 2, Antibody 3, and Antibody 4 are present at mutually adjacent positions on vWF, however, they are different from the epitope for NMC-4.

<7> Inhibitory Effect on Platelet Aggregation in Guinea Pig (ex vivo)

Antibody 2 and Antibody 4 purified in the foregoing item<2> were adjusted to have various concentrations with PBS, and they were intravenously injected into guinea pigs (females, 430 to 600 g) in a dose of 100 μg/kg or 300 μg/kg (one group: 4 guinea pigs). PBS was used as a placebo control. After 5 minutes, blood was collected with citric acid from the abdominal aorta under etherization, from which PRP (number of platelets: $3.0 \times 10^8$ platelets/ml) was prepared to measure RIPA or BIPA in accordance with the same method as described in the item<4>. The parcent inhibition value of each antibody on platelet aggregation was calculated on condition that the maximum aggregation ratio in the PBS-administrated group was regarded to be 100%.

Figure 21:
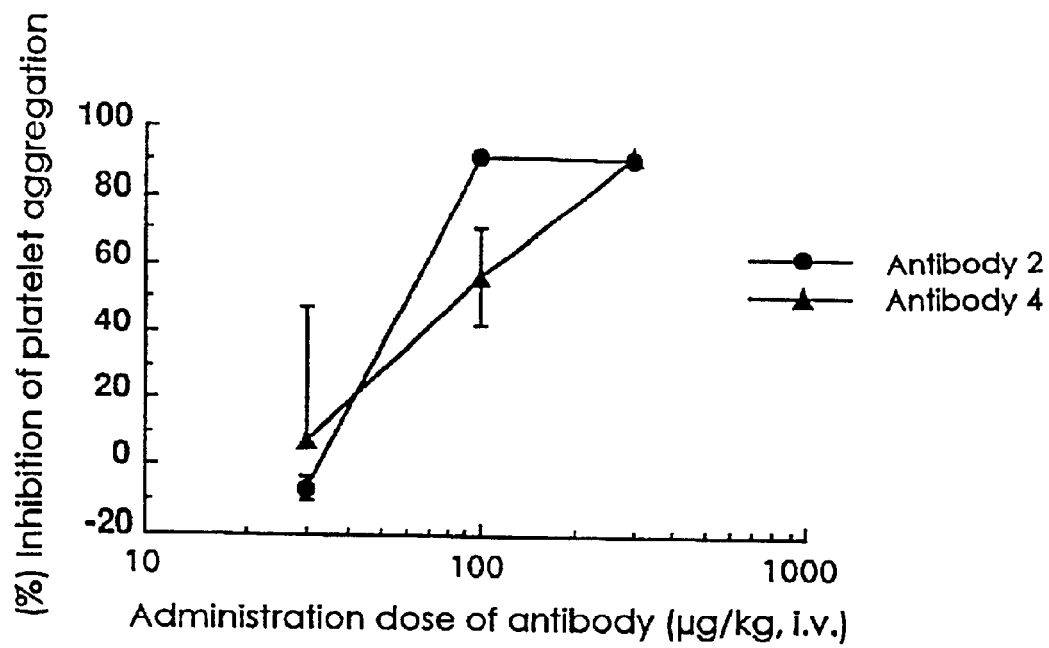
FIG. 21 shows inhibitory effects of Antibody 2 and Antibody 4, measured in ex vivo guinea pig RIPA.
Figure 22:
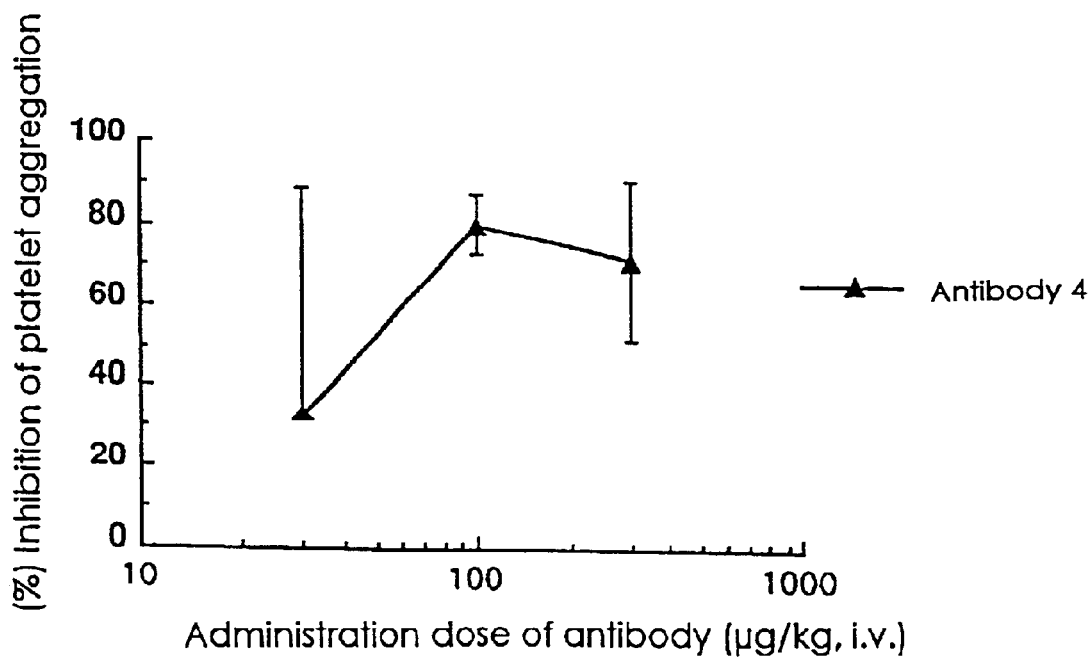
FIG. 22 shows an inhibitory effect of Antibody 4, measured in ex vivo guinea pig BIPA.

Results are shown in FIGS. 21 and 22. Antibody 2 and Antibody 4 inhibited RIPA in a dose-dependent manner.

$ED_{50}$ values (values of 50% inhibition on platelet aggregation) were 70 µg/kg for Antibody 2 and 90 µg/kg for Antibody 4. In BIPA, Antibody 4 had a $ED_{50}$ value of 55 µg/kg. The strong actions of Antibody 2 and Antibody 4 for inhibiting RIPA and BIPA were continuously observed up to 6 hours from the administration, and disappeared after 48 hours.

Separately from the foregoing test, hematological parameters concerning whole blood collected with citric acid after 5 minutes from the administration of the antibody were measured by using an automated hematology analyser (Sysmex E-2000, produced by Toa Medical Electronics). Antibody 2 or Antibody 4 was administered in an administration dose of 100 µg/kg or 300 µg/kg. In any case, no significant variation was observed in total platelet count, total red blood cell count, total white blood cell count, hemoglobin concentration, hematocrit value, mean corpuscular volume, mean corpuscular hemoglobin, mean corpuscular hemoglobin concentration, red blood cell distribution width, platelet distribution width, mean platelet volume, white blood cell large cell ratio, and platelet hematocrit value.

Blood plasma was separated by means of centrifugation operation from blood obtained 5 minutes after the administration of the antibody, in the same manner as described above. The activated partial thromboplastin time, the prothrombin time, and the fibrinogen concentration were measured for the blood plasma by using a coagulation parameter-measuring apparatus (Sysmex CA-3000, produced by Toa Medical Electronics). As a result, no significant variation was observed in the respective parameters even when Antibody 2 or Antibody 4 was administrated in an administration dose of 1000 µg/kg.

<8> Preventive Effects on Thrombus Formation of Monoclonal Antibodies of the Present Invention in Guinea Pig (in vivo)

1) Evaluation of Preventive Effects on Thrombus Formation in Photochemically Induced Thrombus Model in Guinea Pig Carotid Artery (PIT model)

Occlusive thrombus was allowed to be formed in carotid artery of guinea pig in accordance with a method of Nakajima et al. (*Thrombosis Research*, vol. 67, p. 435, 1992) so that the time to thrombus formation was measured with or without administration of Antibody 2 or Antibody 4.

Carotid artery of guinea pig was exposed and exfoliated under urethane anesthesia, to which a probe of pulse Doppler blood flowmeter was installed. Antibody 2, Antibody 4, or physiological saline was administered in an amount of 30, 100, or 300 µg/kg through a cannula attached to the carotid artery. After 5 minutes, a photosensitizing substance, i.e., rose bengal was administered in an amount of 10 mg/kg through the same cannula. Simultaneously, blood vessel located upstream from the probe-installed site (located on a side of the heart) was irradiated with exciting green light at 540 nm by using a thrombus-producing light source (produced by Hamamatsu Photonics) to measure the time (occlusion time) to occlusion of the blood vessel and bloodstream stop due to thrombus formation.

Figure 23:
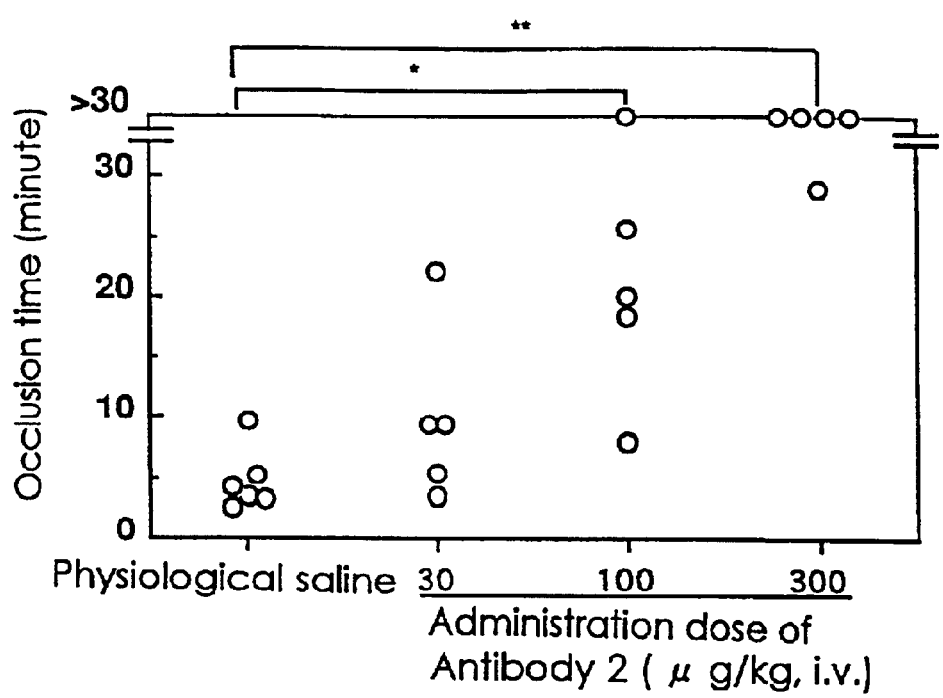
FIG. 23 shows an effect of Antibody 2 on occlusion time in a guinea pig PIT model.
Figure 24:
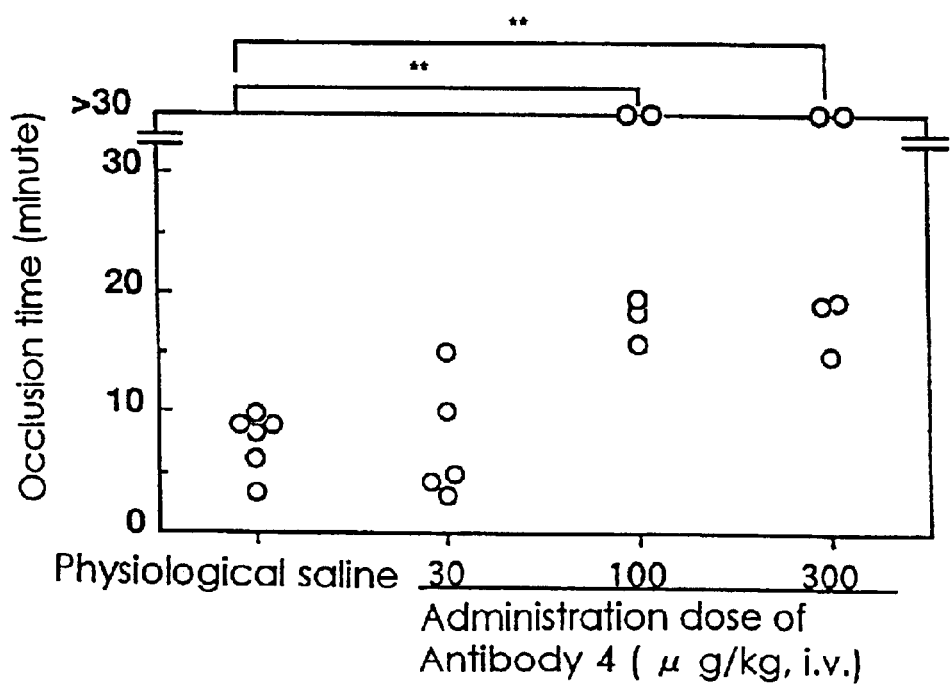
FIG. 24 shows an effect of Antibody 4 on occlusion time in a guinea pig PIT model.

Results are shown in FIGS. 23 and 24. Antibody 2 and Antibody 4 significantly prolonged the occlusion time in an administration dose of not less than 100 µg/kg. Statistical processing was performed by using Mann-Whiteny U test. In FIGS. 23 and 24, a symbol* indicates $p<0.05$, and a symbol** indicates $p<0.01$.

(2) Evaluation of Preventive Effect on Thrombus Formation Based on A-V Shunt Model A polyethylene tube was inserted into left jugular vein of guinea pig under urethane anesthesia, through which Antibody 2 or physiological saline was administered in a dose of 30, 100, or 300 µg/kg. After 5 minutes, an opposite side of the tube was inserted into right jugular vein to form a shunt, and the bloodstream was opened again. The time to bloodstream stop (occlusion time) was measured by using a pulse Doppler blood flowmeter.

Figure 25:
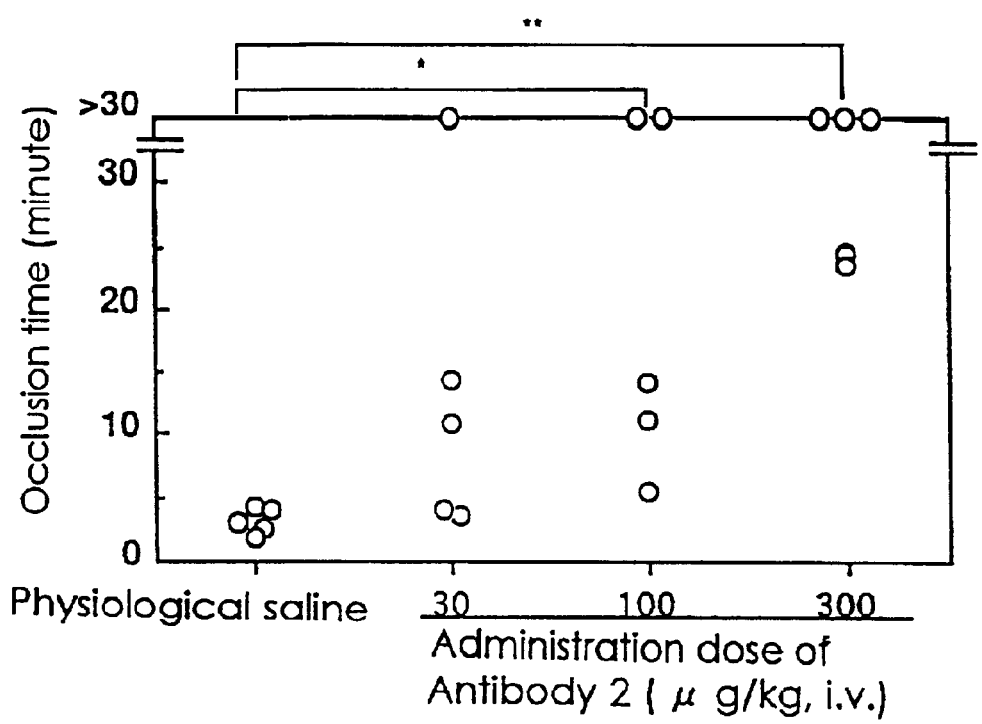
FIG. 25 shows an effect of Antibody 2 on occlusion time in a guinea pig A-V shunt model.

Results are shown in FIG. 25. Antibody 2 significantly prolonged the occlusion time in an administration dose of not less than 100 µg/kg. Statistical processing was performed by using Mann-Whiteny U test. In FIG. 25, a symbol * indicates $p<0.05$, and a symbol ** indicates $p<0.01$.

(3) Evaluation of Prolongation of Bleeding Time

Antibody 2, Antibody 4, or physiological saline was intravenously administered to guinea pig in a dose of 100 or 300 µg/kg under pentobarbital anesthesia. After 5 minutes, planta artery was incised over a length of 5 mm. The presence or absence of bleeding from the wound was confirmed every 15 seconds by using, as an index, a bloodstain adhered to filter paper. The time required from the incision to the stop of bleeding was measured.

Figure 26:
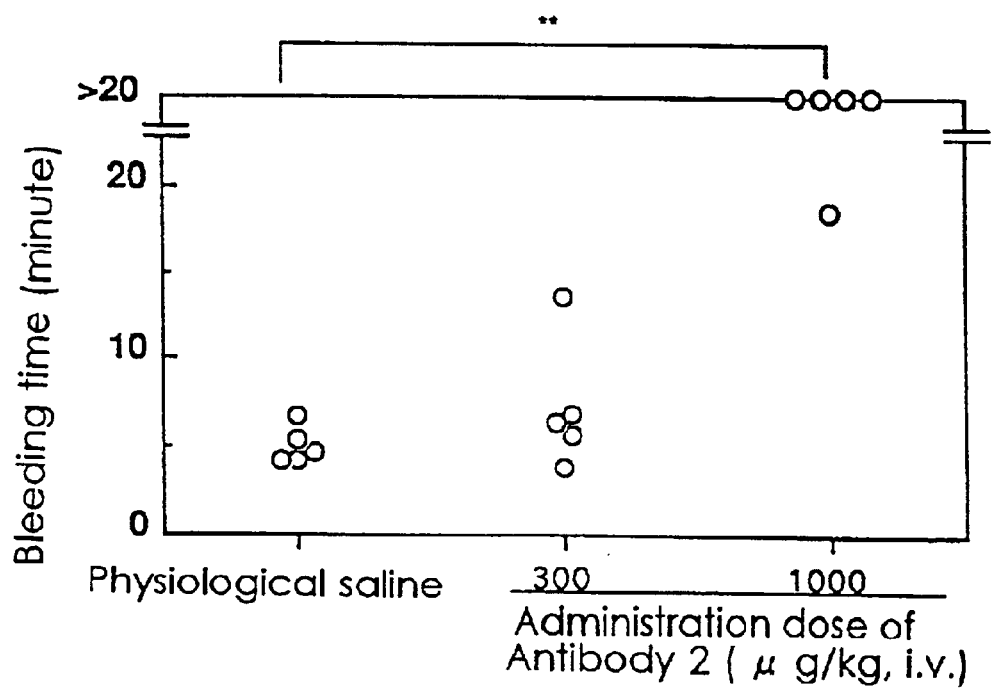
FIG. 26 shows an effect of Antibody 2 on bleeding time in a guinea pig bleeding time model.
Figure 27:
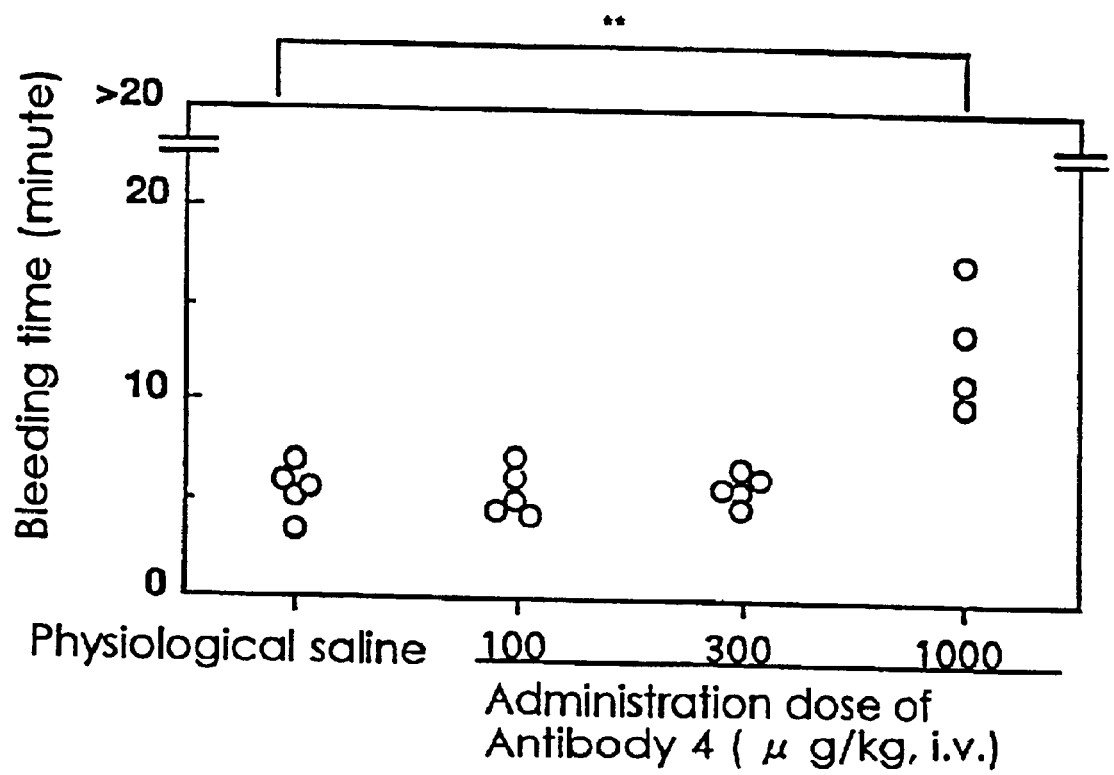
FIG. 27 shows an effect of Antibody 4 on the bleeding time in a guinea pig bleeding time model.

Results are shown in FIGS. 26 and 27. Antibody 2 and Antibody 4 prolonged the bleeding time in a dose of 1000 µg/kg. Antibody 2 and Antibody 4 did not affect the bleeding time at all in an administration dose of 300 µg/kg at which they exhibited the occlusion time-prolonging effect in the PIT model and the A-V shunt model described above. Statistical processing was performed by using Mann-Whiteny U test. In FIGS. 26 and 27, a symbol*indicates $p<0.05$, and a symbol** indicates $p<0.01$.

According to the experimental results described above, it has been demonstrated that both Antibody 2 and Antibody 4 exhibit the strong inhibitory action on thrombus formation without expressing the hemorrhagic tendency which would be otherwise cause clinical problems, when they are administrated to a living body.

INDUSTRIAL APPLICABILITY

The monoclonal antibody obtained according to the present invention has strong affinity and high reaction specificity for vWF, it has an epitope different from those of monoclonal antibodies against vWF having been hitherto known, and it can be used as an active ingredient of an antithrombotic agent. It is expected that the antithrombotic agent of the present invention can be used as a preventive agent and a therapeutic agent extremely effective in diseases relevant to vWF (for example, thrombotic diseases and unstable angina pectoris). Further, extremely useful information on the GPIb-binding site of vWF can be obtained by using the monoclonal antibody of the present invention.

Moreover, the first monoclonal antibody of the present invention has reactivity with guinea pig vWF, and hence it is possible to perform, for example, tests on physiological activities and tests on side effects by using guinea pig.

What is claimed is:

1. A pharmaceutical composition having antithrombotic efficacy comprising a pharmaceutically acceptable carrier and a monoclonal antibody having the following properties:
   (a) the monoclonal antibody binds to human von Willebrand Factor; and
   (b) the monoclonal antibody inhibits binding between a monoclonal antibody produced by hybridoma and human von Willebrand Factor, wherein the hybridoma is selected from the group consisting of FERM BP-5248 (AJvW-2), and FERM BP-5250 (AJvW-4), or a variant of said hybridoma.

2. The pharmaceutical composition according to claim 1, wherein said monoclonal antibody is produced by a hybridoma formed by fusion between mouse myeloma cells and spleen cells of a mouse immunized with human von Willebrand factor.

3. The pharmaceutical composition according to claim 1, wherein the hybridoma is FERM BP-5248 (AJvW-2).

4. The pharmaceutical composition according to claim 1, wherein the hybridoma is a variant of FERM BP-5248 (AJvW-2).

5. The pharmaceutical composition according to claim 1, wherein the hybridoma is FERM BP-5250 (AJvW-4).

6. The pharmaceutical composition according to claim 1, wherein the hybridoma is a variant of FERM BP-5250 (AJvW-4).

7. The pharmaceutical composition according to claim 1, wherein said pharmaceutically acceptable carrier is one or more excipients selected from the group consisting of lactose, potato starch, calcium carbonate, sodium alginate, water, saline, Ringer's solution, and a dispersing agent.

* * * * *

UNITED STATES PATENT AND TRADEMARK OFFICE
CERTIFICATE OF CORRECTION

PATENT NO. : 6,793,920 B2  Page 1 of 1
APPLICATION NO. : 09/923952
DATED : September 21, 2004
INVENTOR(S) : Nagano et al.

It is certified that error appears in the above-identified patent and that said Letters Patent is hereby corrected as shown below:

On the title page, the Terminal Disclaimer information has been omitted. Item (45) and the (*) Notice should read:

-- (45) Date of Patent :   *Sep. 21, 2004 --

(*) Notice: Subject to any disclaimer, the term of this patent is extended or adjusted under 35 U.S.C. 154(b) by 217 days.

This patent is subject to a terminal disclaimer --

On the title page, Item (30), the Foreign Application Priority Data is incorrect. Item (30) should read:

-- (30)   Foreign Application Priority Data

Nov. 30, 1994   (JP) ................................ 6-297070 --

Signed and Sealed this

Twenty-eighth Day of August, 2007

JON W. DUDAS
*Director of the United States Patent and Trademark Office*